US011376057B2

(12) United States Patent
Woloszko et al.

(10) Patent No.: US 11,376,057 B2
(45) Date of Patent: *Jul. 5, 2022

(54) ELECTROSURGICAL METHODS AND SYSTEMS

(71) Applicant: ArthroCare Corporation, Austin, TX (US)

(72) Inventors: Jean Woloszko, Austin, TX (US); Jonathan Gaspredes, Austin, TX (US); David Yuan, Cedar Park, TX (US); Thomas P. Ryan, Austin, TX (US)

(73) Assignee: Arthrocare Corporation, Austin, TX (US)

( * ) Notice: Subject to any disclaimer, the term of this patent is extended or adjusted under 35 U.S.C. 154(b) by 454 days.

This patent is subject to a terminal disclaimer.

(21) Appl. No.: 16/382,674

(22) Filed: Apr. 12, 2019

(65) Prior Publication Data

US 2019/0231412 A1    Aug. 1, 2019

Related U.S. Application Data

(60) Continuation of application No. 15/632,748, filed on Jun. 26, 2017, now Pat. No. 10,448,988, which is a
(Continued)

(51) Int. Cl.
*A61B 18/04* (2006.01)
*A61B 18/14* (2006.01)
(Continued)

(52) U.S. Cl.
CPC ........ *A61B 18/042* (2013.01); *A61B 18/1206* (2013.01); *A61B 18/148* (2013.01);
(Continued)

(58) Field of Classification Search
CPC .. A61B 18/148; A61B 18/042; A61B 18/1206
See application file for complete search history.

(56) References Cited

U.S. PATENT DOCUMENTS

| | | | |
|---|---|---|---|
| 9,713,489 B2 * | 7/2017 | Woloszko | A61B 18/042 |
| 10,448,988 B2 * | 10/2019 | Woloszko | A61B 18/042 |
| 2011/0270242 A1 * | 11/2011 | Marion | A61B 18/148 606/35 |

OTHER PUBLICATIONS

CN Office Action for App No. 201711401138.2 dated Apr. 17, 2020. 7 pages.

* cited by examiner

*Primary Examiner* — Alyssa M Alter
(74) *Attorney, Agent, or Firm* — Norman F. Hainer, Jr.

(57) ABSTRACT

Electrosurgical methods and systems. At least some of the illustrative embodiments are methods including maintaining plasma proximate to an active electrode in a first energy range, and a second energy range. During periods when plasma is proximate to the active electrode, the illustrative method may include controlling flow of fluid drawn into an aperture of an electrosurgical wand, and in some situations increasing fluid flow drawing into the aperture responsive to the active electrode being in operational relationship with tissue, and in other cases decreasing fluid flow drawing into the aperture responsive to the active electrode being in operational relationship with tissue. Further, during periods when plasma is proximate to the active electrode, the illustrative method may include providing output energy at a default energy setpoint, and then providing output energy at a second energy setpoint.

18 Claims, 10 Drawing Sheets

Related U.S. Application Data division of application No. 13/789,973, filed on Mar. 7, 2013, now Pat. No. 9,713,489.

(51) Int. Cl.
*A61B 18/12* (2006.01)
*A61B 18/00* (2006.01)

(52) U.S. Cl.
CPC ............... *A61B 2018/00583* (2013.01); *A61B 2018/00702* (2013.01); *A61B 2018/00744* (2013.01); *A61B 2018/00767* (2013.01); *A61B 2018/00791* (2013.01); *A61B 2018/00827* (2013.01); *A61B 2018/00875* (2013.01); *A61B 2018/00988* (2013.01)

ELECTROSURGICAL METHODS AND SYSTEMS

CROSS-REFERENCE TO RELATED APPLICATIONS

This application is a continuation application of U.S. application Ser. No. 15/632,748 filed Jun. 26, 2017, now U.S. Pat. No. 10,448,988 which is a divisional application of U.S. patent application Ser. No. 13/787,973 filed Mar. 7, 2013, now U.S. Pat. No. 9,713,489 issued Jul. 25, 2017, both entitled "Electrosurgical Methods and Systems", the full disclosures of which are incorporated herein by reference.

BACKGROUND

Electrosurgical systems are used by physicians to perform specific functions during surgical procedures. Particular electrosurgical procedures may remove several different tissue types. For example, procedures involving the knee or shoulder may remove portions of cartilage, meniscus, and free floating and/or trapped tissue. In some cases, the removal may be a very slight removal, such as tissue sculpting, and in other cases the more aggressive removal of tissue is used. Removing each different tissue type, and/or aggressiveness, represents a different amount of applied energy, and in the related-art involves the use of different electrosurgical wands and different electrosurgical controllers. In some cases, a surgeon may forgo use of the correct wand, applied energy, and/or electrosurgical controller to reduce expenses of the procedure, when better clinical results may have been achieved using multiple electrosurgical wands, energies, and/or controllers.

Any advance that makes treatment easier for the surgeon, and achieves better results, would provide a competitive advantage.

BRIEF DESCRIPTION OF THE DRAWINGS

For a detailed description of exemplary embodiments, reference will now be made to the accompanying drawings in which.

NOTATION AND NOMENCLATURE

Figure 1:
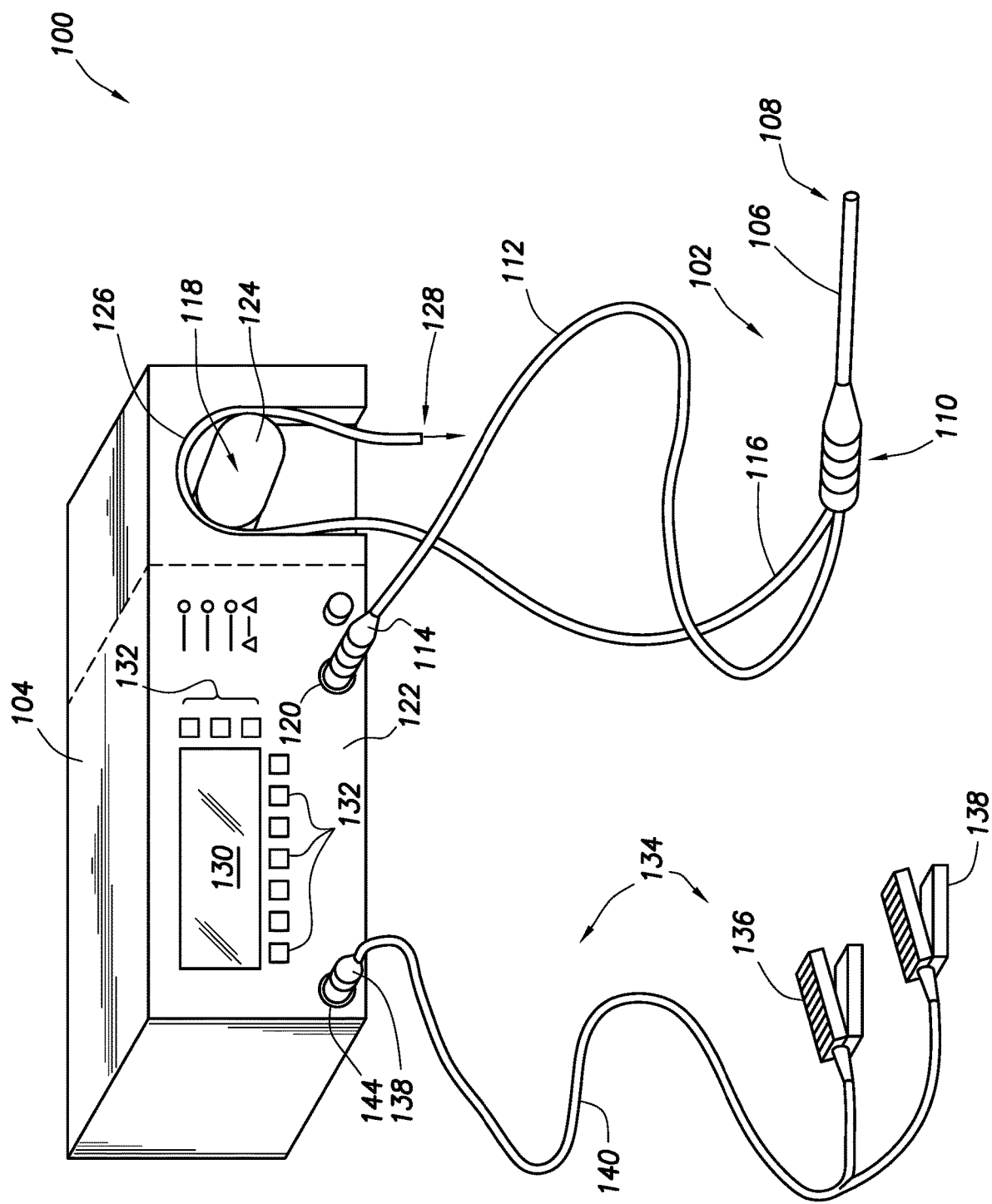
FIG. 1 shows an electrosurgical system in accordance with at least some embodiments.

Certain terms are used throughout the following description and claims to refer to particular system components. As one skilled in the art will appreciate, companies that design and manufacture electrosurgical systems may refer to a component by different names. This document does not intend to distinguish between components that differ in name but not function.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

Reference to a singular item includes the possibility that there are plural of the same items present. More specifically, as used herein and in the appended claims, the singular forms "a," "an," "said" and "the" include plural references unless the context clearly dictates otherwise. It is further noted that the claims may be drafted to exclude any optional element. As such, this statement serves as antecedent basis for use of such exclusive terminology as "solely," "only" and the like in connection with the recitation of claim elements, or use of a "negative" limitation. Lastly, it is to be appreciated that unless defined otherwise, all technical and scientific terms used herein have the same meaning as commonly understood by one of ordinary skill in the art to which this invention belongs.

"Plasma" shall mean a low temperature gas formed of vapor bubbles or a vapor layer that is capable of emitting an ionized discharge.

"Ablation" shall mean removal of tissue based on tissue interaction with a plasma.

"Mode of ablation" shall refer to one or more characteristics of an ablation. Lack of ablation (i.e., a lack of plasma) shall not be considered a "mode of ablation." A mode which performs coagulation shall not be considered a "mode of ablation."

"Active electrode" shall mean an electrode of an electrosurgical wand which produces an electrically-induced tissue-altering effect when brought into contact with, or close proximity to, a tissue targeted for treatment.

"Return electrode" shall mean an electrode of an electrosurgical wand which serves to provide a current flow path for electrical charges with respect to an active electrode, and/or an electrode of an electrical surgical wand which does not itself produce an electrically-induced tissue-altering effect on tissue targeted for treatment.

"Electric motor" shall include alternating current (AC) motors, direct current (DC) motors, as well as stepper motors.

"Controlling flow of fluid" shall mean controlling a volume flow rate. Control of applied pressure to maintain a set point pressure (e.g., suction pressure) independent of volume flow rate of liquid caused by the applied pressure shall not be considered "controlling flow of fluid." However, varying applied pressure to maintain a set point volume flow rate of liquid shall be considered "controlling flow of fluid".

"Output energy" and "output RF energy" shall refer to the rate at which electrical energy is provided, transferred, or used over time.

"Energy range" shall refer to a lower limit output energy, upper limit output energy, and all the intervening output energies between the lower limit and the upper limit. A first energy range and a second energy range may overlap (e.g., the lower limit of the second energy range may be an intervening energy in the first energy range), but so long as at least a portion of each energy range is mutually exclusive, the two energy ranges shall be considered distinct for purposes of the specification and claims.

"Energy setpoint" shall refer to a specific output energy that falls within an energy range.

A proximity that is in "operational relationship with tissue" shall mean a proximity wherein the tissue interacting with a plasma affects the impedance presented by the plasma and surrounding fluid to electrical current flow through the plasma and surrounding fluid.

A fluid conduit said to be "within" an elongate shaft shall include not only a separate fluid conduit that physically resides within an internal volume of the elongate shaft, but also situations where the internal volume of the elongate shaft is itself the fluid conduit.

Where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

DETAILED DESCRIPTION

Before the various embodiments are described in detail, it is to be understood that this invention is not limited to particular variations set forth herein as various changes or modifications may be made, and equivalents may be substituted, without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

The various embodiments are directed to electrosurgical methods and related electrosurgical systems. In particular, the various embodiments are directed to an electrosurgical system having multiple modes of ablation that are configured for treatment of a specific targeted tissue type or electrosurgical effect desired, and implemented by a single electrosurgical wand and a single electrosurgical controller. In example embodiments, the multiple modes of ablation are implemented by a single active electrode on the electrosurgical wand, and within each mode multiple energy setpoints may be implemented. The specification first turns to an illustrative system to orient the reader.

FIG. 1 illustrates an electrosurgical system 100 in accordance with at least some embodiments. In particular, the electrosurgical system 100 comprises an electrosurgical wand 102 (hereinafter "wand 102") coupled to an electrosurgical controller 104 (hereinafter "controller 104"). The wand 102 comprises an elongate shaft 106 that defines distal end 108. The elongate shaft 106 further defines a handle or proximal end 110, where a physician grips the wand 102 during surgical procedures. The wand 102 further comprises a flexible multi-conductor cable 112 housing one or more electrical leads (not specifically shown in FIG. 1), and the flexible multi-conductor cable 112 terminates in a wand connector 114. As shown in FIG. 1, the wand 102 couples to the controller 104, such as by a controller connector 120 on an outer surface of the enclosure 122 (in the illustrative case of FIG. 1, the front surface).

Though not visible in the view of FIG. 1, in some embodiments the wand 102 has one or more internal fluid conduits coupled to externally accessible tubular members. As illustrated, the wand 102 has a flexible tubular member 116, used to provide aspiration at the distal end 108 of the wand. In accordance with various embodiments, the tubular member 116 couples to a peristaltic pump 118, which peristaltic pump 118 is illustratively shown as an integral component with the controller 104 (i.e., residing at least partially within the enclosure 122 of the controller 104). In other embodiments, an enclosure for the peristaltic pump 118 may be separate from the enclosure 122 for the controller 104 (as shown by dashed lines in the figure), but in any event the peristaltic pump is operatively coupled to the controller 104.

The peristaltic pump 118 comprises a rotor portion 124 (hereafter just "rotor 124") as well as a stator portion 126 (hereafter just "stator 126"). The flexible tubular member 116 couples within the peristaltic pump 118 between the rotor 124 and the stator 126, and movement of the rotor 124 against the flexible tubular member 116 causes fluid movement toward the discharge 128. While the illustrative peristaltic pump 118 is shown with a two-head rotor 124, varying types of peristaltic pumps 118 may be used (e.g., a five-head peristaltic pump). In the context of the various embodiments, the peristaltic pump 118 creates a volume-controlled aspiration from a surgical field at the distal end 108 of the wand 102, with the control based on a speed of the rotor 124, as commanded by the controller 104.

Still referring to FIG. 1, a display device or interface device 130 is visible through the enclosure 122 of the controller 104, and in some embodiments a user may select operational modes of the controller 104 by way of the interface device 130 and related buttons 132. For example, using one or more of the buttons 132 the surgeon may select among modes of ablation, such as: a low mode which may be used for removal of portions of cartilage; a medium mode which may be used for removal of meniscus; a high mode for aggressive removal of tissue; and a vacuum mode for removal free floating and/or trapped tissue. The various modes of ablation are discussed more thoroughly below.

In some embodiments the electrosurgical system 100 also comprises a foot pedal assembly 134. The foot pedal assembly 134 may comprise one or more pedal devices 136 and 138, a flexible multi-conductor cable 140 and a pedal connector 142. While only two pedal devices 136 and 138 are shown, one or more pedal devices may be implemented. The enclosure 122 of the controller 104 may comprise a corresponding connector 144 that couples to the pedal connector 142. A physician may use the foot pedal assembly 134 to control various aspects of the controller 104, such as the mode of ablation. For example, pedal device 136 may be used for on-off control of the application of radio frequency (RF) output energy to the wand 102, and more specifically for control of output energy in a mode of ablation. Further, pedal device 138 may be used to control and/or set the mode of ablation of the electrosurgical system. For example, actuation of pedal device 138 may switch between energy levels created by the controller 104 and aspiration volume created by the peristaltic pump 118. In certain embodiments, control of the various operational or performance aspects of controller 104 may be activated by selectively depressing finger buttons located on handle 110 of wand 102 (the finger buttons not specifically shown so as not to unduly complicate the figure).

The electrosurgical system 100 of the various embodiments may have a variety of modes of ablation which employ Coblation® technology. In particular, the assignee of the present disclosure is the owner of Coblation® technology. Coblation® technology involves the application of a radio frequency (RF) signal between one or more active electrodes and one or more return electrodes of the wand 102 to develop high electric field intensities in the vicinity of the target tissue. The electric field intensities may be sufficient to vaporize an electrically conductive fluid over at least a portion of the one or more active electrodes in the region between the one or more active electrodes and the target tissue. The electrically conductive fluid may be inherently present in the body, such as blood, or in some cases extracellular or intracellular fluid. In other embodiments, the electrically conductive fluid may be a liquid or gas, such as isotonic saline. In some embodiments, such as surgical procedures involving a knee or shoulder, the electrically conductive fluid is delivered in the vicinity of the active electrode and/or to the target site by a delivery system separate and apart from the system 100.

When the electrically conductive fluid is heated to the point that the atoms of the fluid vaporize faster than the atoms recondense, a gas is formed. When sufficient energy is applied to the gas, the atoms collide with each other causing a release of electrons in the process, and an ionized gas or plasma is formed (the so-called "fourth state of matter"). Stated otherwise, plasmas may be formed by heating a gas and ionizing the gas by driving an electric current through the gas, or by directing electromagnetic waves into the gas. The methods of plasma formation give energy to free electrons in the plasma directly, electron-atom collisions liberate more electrons, and the process cascades until the desired degree of ionization is achieved. A more complete description of plasma can be found in Plasma Physics, by R. J. Goldston and P. H. Rutherford of the Plasma Physics Laboratory of Princeton University (1995), the complete disclosure of which is incorporated herein by reference.

As the density of the plasma becomes sufficiently low (i.e., less than approximately 1020 atoms/cm$^3$ for aqueous solutions), the electron mean free path increases such that subsequently injected electrons cause impact ionization within the plasma. When the ionic particles in the plasma layer have sufficient energy (e.g., 3.5 electron-Volt (eV) to 5 eV), collisions of the ionic particles with molecules that make up the target tissue break molecular bonds of the target tissue, dissociating molecules into free radicals which then combine into gaseous or liquid species. By means of the molecular dissociation (as opposed to thermal evaporation or carbonization), the target tissue is volumetrically removed through molecular dissociation of larger organic molecules into smaller molecules and/or atoms, such as hydrogen, oxygen, oxides of carbon, hydrocarbons and nitrogen compounds. The molecular dissociation completely removes the tissue structure, as opposed to dehydrating the tissue material by the removal of liquid within the cells of the tissue and extracellular fluids, as occurs in related art electrosurgical desiccation and vaporization. A more detailed description of the molecular dissociation can be found in commonly assigned U.S. Pat. No. 5,697,882 the complete disclosure of which is incorporated herein by reference.

The energy density produced by electrosurgical system 100 at the distal end 108 of the wand 102 may be varied by adjusting a variety of factors, such as: the number of active electrodes; electrode size and spacing; electrode surface area; asperities and/or sharp edges on the electrode surfaces; electrode materials; applied voltage; current limiting of one or more electrodes (e.g., by placing an inductor in series with an electrode); electrical conductivity of the fluid in contact with the electrodes; density of the conductive fluid; and other factors. Accordingly, these factors can be manipulated to control the energy level of the excited electrons. Since different tissue structures have different molecular bonds, the electrosurgical system 100 may be configured to produce energy sufficient to break the molecular bonds of certain tissue but insufficient to break the molecular bonds of other tissue. For example, fatty tissue (e.g., adipose) has double bonds that require an energy level higher than 4 eV to 5 eV (i.e., on the order of about 8 eV) to break. Accordingly, the Coblation® technology in some modes of operation does not ablate such fatty tissue; however, the Coblation® technology at the lower energy levels may be used to effectively ablate cells to release the inner fat content in a liquid form. Other modes of operation may have increased energy such that the double bonds can also be broken in a similar fashion as the single bonds (e.g., increasing voltage or changing the electrode configuration to increase the current density at the electrodes). A more complete description of the various phenomena can be found in commonly assigned U.S. Pat. Nos. 6,355,032; 6,149,120 and 6,296,136, the complete disclosures of which are incorporated herein by reference.

The inventors now present a theoretical underpinning to explain how multiple modes of ablation may be implemented with a single wand 102 and a single controller 104. However, the theoretical basis is presented merely as one possible explanation, and shall not be read as a limitation on the operation of the various embodiments. Another theoretical basis may be equivalently proffered, and attempting to explain operation of a device using a different theoretical basis shall not obviate whether such a device falls within the appended claims. In particular, the electrode circuit, including the plasma created and maintained in operational relationship to an active electrode of a wand, the fluid between the active and return electrode, and the electrode-fluid interface, has or presents a certain amount of impedance to the flow of output energy away from the active electrode toward a return electrode. The impedance presented by the electrode circuit may be dependent on many factors, including but not limited to the thickness and volume of the plasma itself, the surface area of the active electrode not covered by a vapor layer and directly in contact with the conductive fluid, and the volume flow of fluid and/or gasses away from the location of the plasma.

In related-art devices, only the vacuum pressure used for aspiration is controlled (e.g., the vacuum available at wall socket connections in a hospital operating room). However, the vacuum available at a wall socket connection may be highly variable from room to room, and in many cases within the same room over time. Moreover, control of vacuum pressure applied does not imply a controlled volume of aspiration. Thus, while related-art devices may control vacuum pressure, they do not control volume flow rate of the aspiration.

The inventors have found that the relationship of the volume of flow of fluid of the aspiration to output energy dissipation is counter to the prevailing understanding. That is, related-art devices and methods operate under the assumption that a generally high flow rate more rapidly carries away output energy and thus reduces thermal aspects of the ablation. By contrast, the inventors have found that high volume flow of aspiration tends to cause higher output energy dissipation overall. With respect to the plasma, the inventors have found that higher volume flow rates drive both the impedance of the plasma and of the electrode circuit down, which increases the output energy dissipation. Moreover, higher volume flow rates cause the plasma to "flicker". Consider an analogy in the form of a candle. If a candle is burning in a room with very little air movement, the flame may be a steady shape, size, and location. However, in the presence of airflow (e.g., a ceiling fan), the flame tends to "flicker". If one considers that during periods of time of plasma collapse (i.e., absence of plasma) greater output energy is dissipated in a thermal mode through the surrounding fluid and tissue, "flickering" plasma caused by high volume flow rate may result in more output energy dissipation in the tissue and surrounding fluid, rather than less. That is, not only will the "flickering" plasma present a lower average impedance and thus higher output energy dissipation, but also the thermal mode that dominates during momentary plasma collapse present in "flicker" causes higher output energy dissipation than periods of time when plasma is present.

The finding that the volume flow of fluid of the aspiration is proportional to output energy dissipation is counter to the prevailing understanding. That is, related-art devices and methods operate under the assumption that a generally high flow rate more rapidly carries away output energy and thus reduces thermal aspects of the ablation. By contrast, the inventors have found that high volume flow of aspiration tends to cause higher output energy dissipation overall. With respect to the plasma, the inventors have found that higher volume flow rates drive the impedance of the plasma down, which increases the output energy dissipation. Moreover, higher volume flow rates cause the plasma to "flicker". Consider an analogy in the form of a candle. If a candle is burning in a room with very little air movement, the flame may be a steady shape, size, and location. However, in the presence of airflow (e.g., a ceiling fan), the flame tends to "flicker". If one considers that during periods of time of plasma collapse (i.e., absence of plasma) greater output energy is dissipated in a thermal mode through the surrounding fluid and tissue, "flickering" plasma caused by high volume flow rate may result in more output energy dissipation in the tissue and surrounding fluid, rather than less. That is, not only will the "flickering" plasma present a lower average impedance and thus higher output energy dissipation, but also the thermal mode that dominates during momentary plasma collapse present in "flicker" causes higher output energy dissipation than periods of time when plasma is present.

Accordingly, the embodiments described herein are related to a system wherein the impedance at the electrode is (directly or indirectly) monitored and used as a parameter to control the volume flow rate of aspiration in order to control the plasma field in a way that is desirable for a specific tissue type or procedure. For example, in some modes of ablation if the impedance at the active electrode is observed to decrease at a point during a procedure (possibly indicating plasma instability), the system may direct the peristaltic pump to decrease the aspiration flow rate to enable the plasma field to stabilize. From another perspective, it may be desirable to measure the RF electrical current applied to the active electrode and adjust the peristaltic pump (and thus the fluid flow) in order to keep the RF electrical current at a certain predetermined and desired level associated with the mode of ablation. Reference is also made to commonly assigned U.S. Pat. No. 8,192,424, titled "ELECTROSURGICAL SYSTEM WITH SUCTION CONTROL APPARATUS, SYSTEM AND METHOD" the complete disclosure of which is incorporated herein by reference for all purposes. Conversely, it may be desirable in certain modes of ablation to trade off plasma field stability in order to have higher overall aspiration fluid flow volume in order to remove bubbles and debris from the surgical field.

Based on the theoretical underpinning in the paragraphs above, the various embodiments are directed to systems and related methods implementing at least two modes of ablation during an electrosurgical procedure, in some embodiments using a single wand (and in some cases a single active electrode) along with a single controller. In a particular embodiment, four different modes of ablation may be implemented, such as: a "low mode" which may be used for the treatment and removal of portions of sensitive tissue such as portions of articular cartilage; a "medium mode" which may be used for the treatment and removal of meniscus; a "high mode" for aggressive removal of tissue of any kind; and a "vacuum mode" for removal free floating and/or trapped tissue. Moreover, some example systems implement multiple energy/flow setpoints within a single mode of ablation. For example, the "low mode" of ablation may comprise a default setpoint energy/flow, but a surgeon may choose an increased energy/flow setpoint within the energy range associated with the "low mode" of ablation. Likewise, the surgeon may choose a decreased energy/flow setpoint in relation to the default setpoint yet still within the energy range associated with the "low mode" of ablation. More detail regarding the illustrative modes of ablation, and setpoints within each mode, is presented below, after a discussion of an illustrative wand 102 and internal components of the controller 104.

Figure 2:
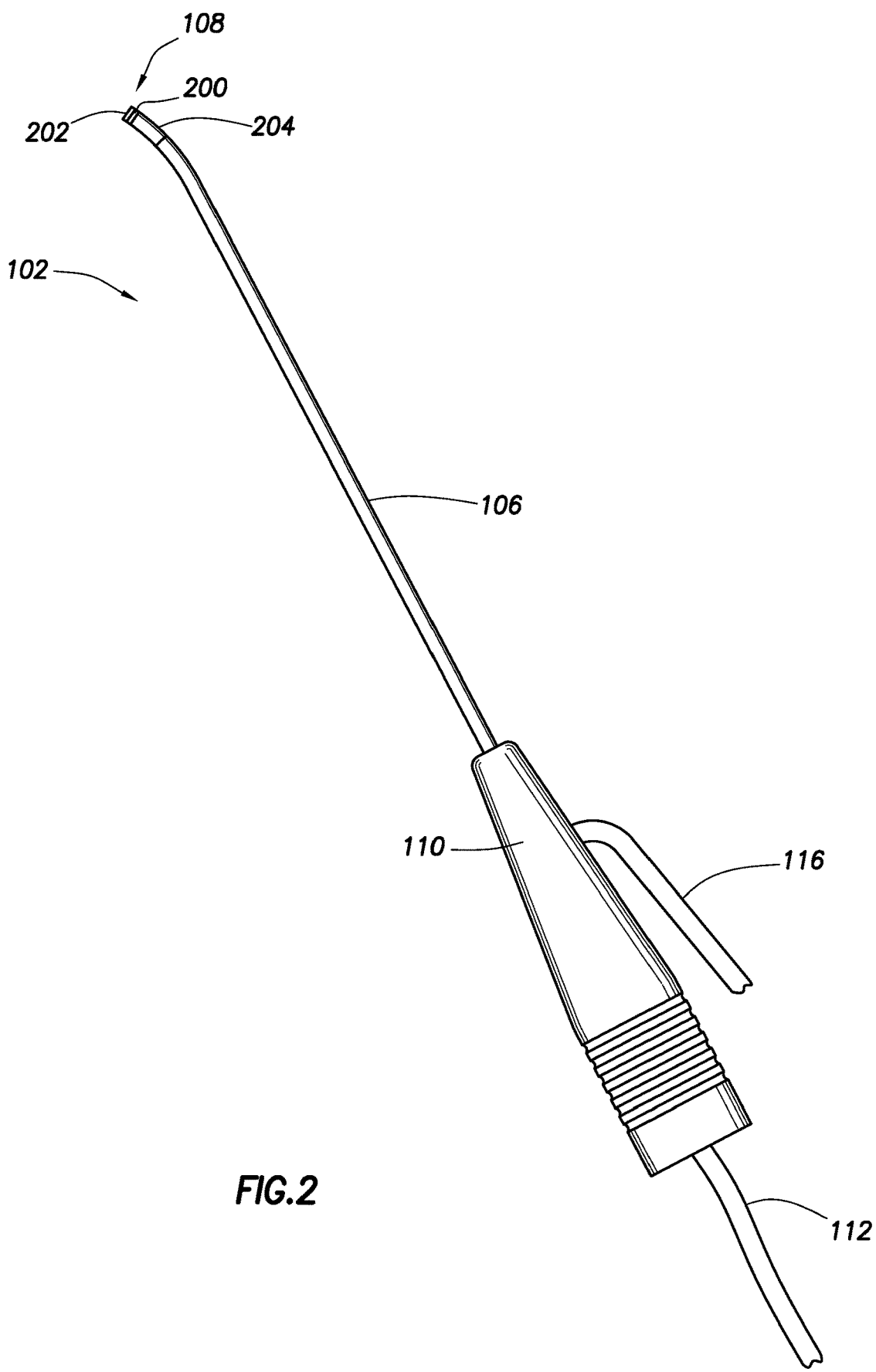
FIG. 2 shows an elevation view of an electrosurgical wand in accordance with at least some embodiments.

FIG. 2 shows an elevation view of wand 102 in accordance with example systems. In particular, wand 102 comprises elongate shaft 106 which may be flexible or rigid, a handle 110 coupled to the proximal end of the elongate shaft 106, and an electrode support member 200 coupled to the distal end of elongate shaft 106. Also visible in FIG. 2 is the flexible tubular member 116 extending from the wand 102 and the multi-conductor cable 112. The wand 102 comprises an active electrode 202 disposed on the distal end 108 of the elongate shaft 106. Active electrode 202 may be coupled to an active or passive control network within controller 104 (FIG. 1) by means of one or more insulated electrical connectors (not shown) in the multi-conductor cable 112. The active electrode 202 is electrically isolated from a common or return electrode 204 which is disposed on the shaft proximally of the active electrode 202, in some example systems within 1 millimeter (mm) to 25 mm of the distal tip. Proximally from the distal tip, the return electrode 204 is concentric with the elongate shaft 106 of the wand 102. The support member 200 is positioned distal to the return electrode 204 and may be composed of an electrically insulating material such as epoxy, plastic, ceramic, silicone, glass or the like. Support member 200 extends from the distal end 108 of elongate shaft 106 (usually about 1 to 20 mm) and provides support for active electrode 202.

Figure 3:
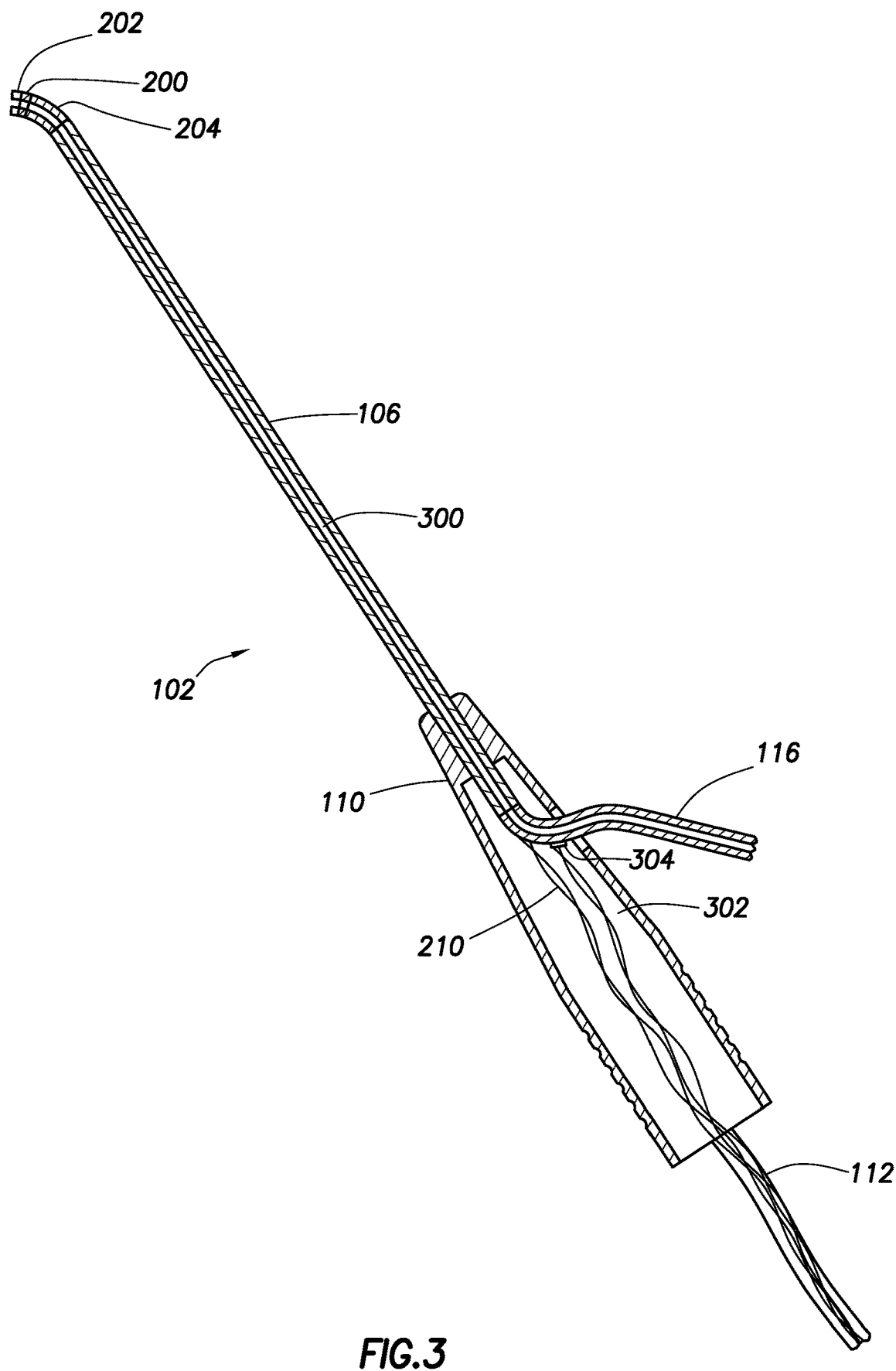
FIG. 3 shows a cross-sectional elevation view of an electrosurgical wand in accordance with at least some embodiments.

FIG. 3 shows a cross-sectional elevation view of the wand 102 in accordance with example embodiments. In particular, wand 102 comprises a suction lumen 300 defined within the elongate shaft 106. In the example wand 102 of FIG. 3, the inside diameter of the elongate shaft 106 defines the section lumen 300, but in other cases a separate tubing within the elongate shaft 106 may define the suction lumen 300. The suction lumen 300 may be used for aspirating excess fluids, bubbles, tissue fragments, and/or products of ablation from the target site proximate to the active electrode 202. Suction lumen 300 extends into the handle 110 and fluidly couples to the flexible tubular member 116 for coupling to the peristaltic pump 118. Handle 110 also defines an inner cavity 302 within which electrical conductors 210 may reside, where the electrical conductors 210 may extend into the multi-conductor cable 112 and ultimately couple to the controller 104. The electrical conductors likewise extend through the elongate shaft and couple, one each, to the return electrode 204 and the active electrode 202, but the electrical conductors 210 are not shown to reside within the elongate shaft 106 so as not to unduly complicate the figure.

In some systems, the wand 102 may further comprise a temperature measurement device 304 in operational relationship to the flexible tubular member 116. As illustrated in FIG. 3, the temperature measurement device resides within the inner cavity 302 defined by the handle 110, but the temperature measurement device may be placed at any suitable location. The temperature measurement device 304 is used to directly or indirectly measure the temperature of the fluid within the tubular member 116. As illustrated, the temperature measurement device 304 abuts an outer surface of the tubular member 116 such that as fluids travel within the tubular member 116 past the location of the temperature measurement device 304, localized temperature changes can be read. The temperature measurement device 304 may take any suitable form, such as a resistive thermal device (RTD), a thermistor, an optical temperature probe, or a thermocouple. The temperature measurement device may be useful in a variety of operational circumstances, such as clog detection discussed more below.

Figure 4:
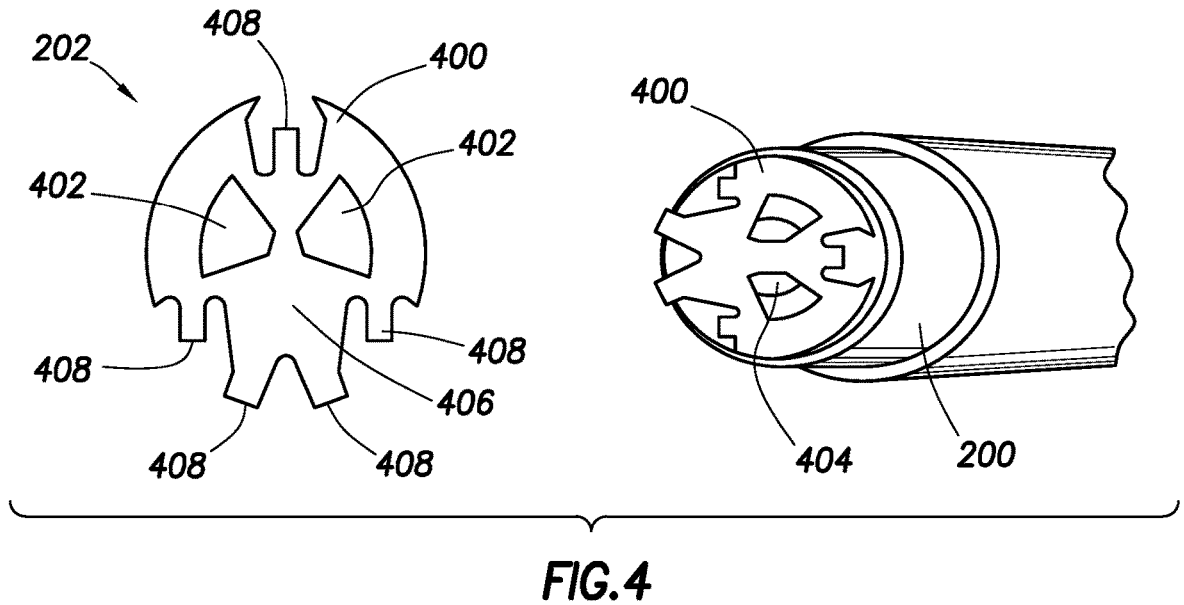
FIG. 4 shows both an elevation view of screen electrode, and a perspective view of a distal end of an electrosurgical wand comprising the screen electrode, in accordance with at least some embodiments.

FIG. 4 shows an elevation view of an example active electrode (on the left), as well as a perspective view of the distal end of wand 102 (on the right), in accordance with example systems. In particular, active electrode 202 may be an active screen electrode 400 as shown in FIG. 4. Screen electrode 400 may comprise a conductive material, such as tungsten, titanium, molybdenum, platinum, or the like. Screen electrode 400 may have a diameter in the range of about 0.5 to 8 mm, in some cases about 1 to 4 mm, and a thickness of about 0.05 to about 2.5 mm, in some cases about 0.1 to 1 mm. Screen electrode 400 may comprise a plurality of apertures 402 configured to rest over an aperture or distal opening 404 of the suction lumen. Apertures 402 are designed to enable the passage of aspirated excess fluids, bubbles, and gases from the ablation site and are large enough to enable ablated tissue fragments to pass through into suction lumen 206 (FIG. 3). As shown, screen electrode 400 has an irregular shape which increases the edge to surface-area ratio of the screen electrode 400. A large edge to surface-area ratio increases the ability of screen electrode 400 to initiate and maintain a plasma layer in conductive fluid because the edges generate higher current densities, which a large surface area electrode tends to dissipate power into the conductive media.

In the representative embodiment shown in FIG. 4, screen electrode 400 comprises a body 406 that rests over insulative support member 200 and the distal opening 404 to suction lumen 206. Screen electrode 400 further comprises tabs 408, in the example screen electrode 400 of FIG. 4, five tabs 408 are shown. The tabs 408 may rest on, be secured to, and/or be embedded in insulative support member 200. In certain embodiments, electrical connectors extend through insulative support member 200 and are coupled (i.e., via adhesive, braze, weld, or the like) to one or more of tabs 408 in order to secure screen electrode 400 to the insulative support member 200 and to electrically couple screen electrode 400 to controller 104 (FIG. 1). In example systems, screen electrode 400 forms a substantially planar tissue treatment surface for smooth resection, ablation, and sculpting of the meniscus, cartilage, and other tissues. In reshaping cartilage and meniscus, the physician often desires to smooth the irregular and ragged surface of the tissue, leaving behind a substantially smooth surface. For these applications, a substantially planar screen electrode treatment surface provides the desired effect. The specification now turns to a more detailed description of the controller 104.

Figure 5:
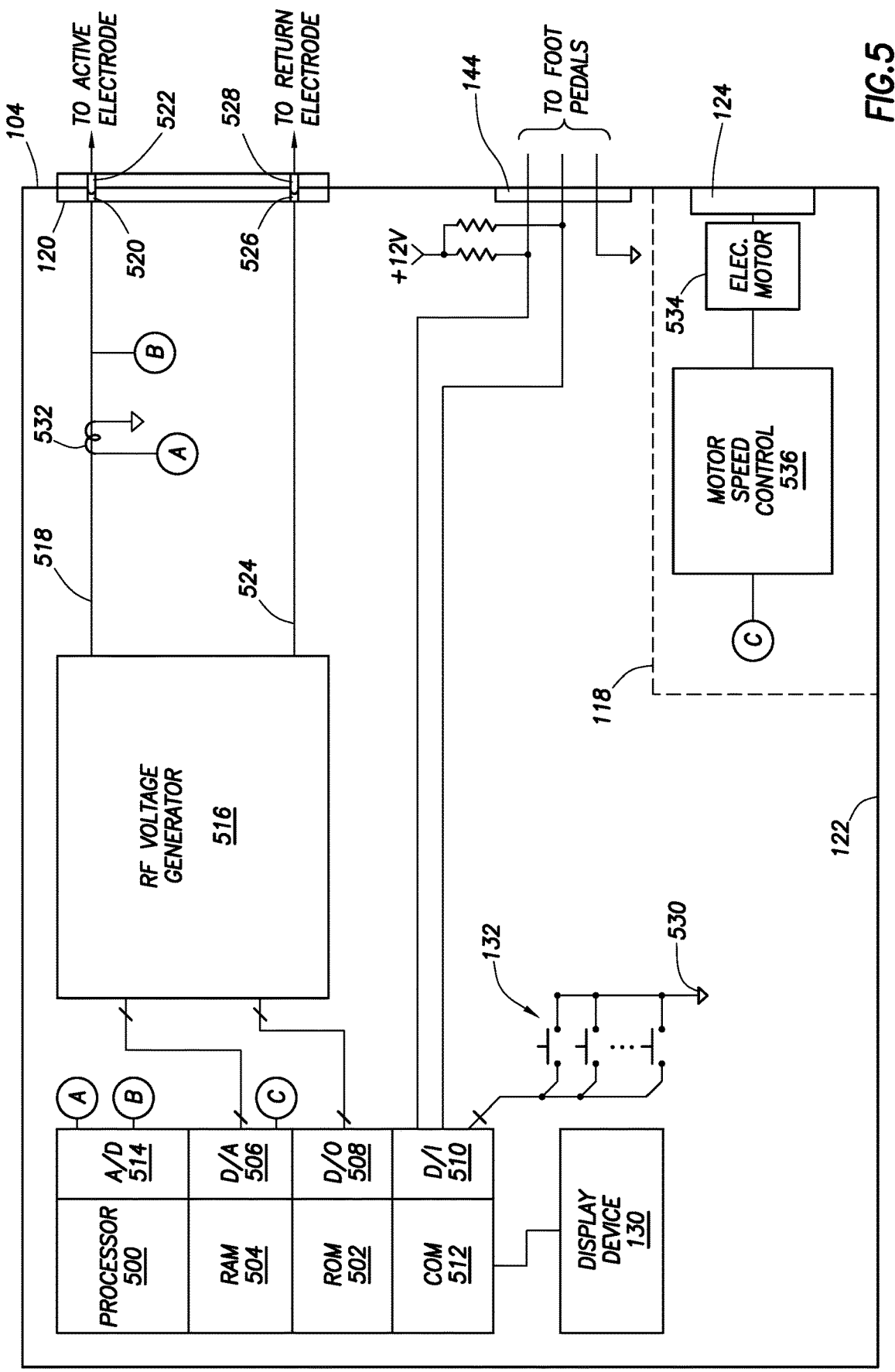
FIG. 5 shows an electrical block diagram of a controller in accordance with at least some embodiments.

FIG. 5 shows an electrical block diagram of controller 104 in accordance with at least some embodiments. In particular, the controller 104 comprises a processor 500. The processor 500 may be a microcontroller, and therefore the microcontroller may be integral with read-only memory (ROM) 502, random access memory (RAM) 504, digital-to-analog converter (D/A) 506, analog-to-digital converter (A/D) 514, digital outputs (D/O) 508, and digital inputs (D/I) 510. The processor 500 may further provide one or more externally available peripheral busses, such as a serial bus (e.g., $I^2C$), parallel bus, or other bus and corresponding communication mode. The processor 500 may further be integral with communication logic 512 to enable the processor 500 to communicate with external devices, as well as internal devices, such as display device 130. Although in some embodiments the processor 500 may be implemented in the form of a microcontroller, in other embodiments the processor 500 may be implemented as a standalone central processing unit in combination with individual RAM, ROM, communication, A/D, D/A, D/O, and D/I devices, as well as communication hardware for communication to peripheral components.

ROM 502 stores instructions executable by the processor 500. In particular, the ROM 502 may comprise a software program that, when executed, causes the controller to implement two or more modes of ablation, including increasing and decrease peristaltic pump speed responsive to various feedback parameters (discussed more below). The RAM 504 may be the working memory for the processor 500, where data may be temporarily stored and from which instructions may be executed. Processor 500 couples to other devices within the controller 104 by way of the digital-to-analog converter 506 (e.g., in some embodiment the RF voltage generator 516), digital outputs 508 (e.g., in some embodiment the RF voltage generator 516), digital inputs 510 (e.g., interface devices such as push button switches 132 or foot pedal assembly 134 (FIG. 1)), and communication device 512 (e.g., display device 130).

Voltage generator 516 generates an alternating current (AC) voltage signal that is coupled to active electrode 202 of the wand 102 (FIG. 3). In some embodiments, the voltage generator defines an active terminal 518 which couples to electrical pin 520 in the controller connector 120, electrical pin 522 in the wand connector 114, and ultimately to the active electrode 202 (FIG. 3). Likewise, the voltage generator defines a return terminal 524 which couples to electrical pin 526 in the controller connector 120, electrical pin 528 in the wand connector 114, and ultimately to the return electrode 204 (also see FIG. 3). Additional active terminals and/or return terminals may be used. The active terminal 518 is the terminal upon which the voltages and electrical currents are induced by the voltage generator 516, and the return terminal 524 provides a return path for electrical currents. It would be possible for the return terminal 524 to provide a common or ground being the same as the common or ground within the balance of the controller 104 (e.g., the common 530 used on push-buttons 132), but in other embodiments the voltage generator 516 may be electrically "floated" from the balance of the controller 104, and thus the return terminal 524, when measured with respect to the common or earth ground (e.g., common 530) may show a voltage; however, an electrically floated voltage generator 516 and thus the potential for voltage readings on the return terminals 524 relative to earth ground does not negate the return terminal status of the terminal 524 relative to the active terminal 518.

The AC voltage signal generated and applied between the active terminal 518 and return terminal 524 by the voltage generator 516 is RF energy that, in some embodiments, has a frequency of between about 5 kilo-Hertz (kHz) and 20 Mega-Hertz (MHz), in some cases being between about 30 kHz and 2.5 MHz, in other cases being between about 50 kHz and 500 kHz, often less than 350 kHz, and often between about 100 kHz and 200 kHz. In some applications, a frequency of about 100 kHz is useful because target tissue impedance is greater at 100 kHz.

The RMS (root mean square) voltage generated by the voltage generator 516 may be in the range from about 5 Volts (V) to 1800 V, in some cases in the range from about 10 V to 500 V, often between about 10 V to 400 V depending on the mode of ablation and active electrode size. The peak-to-peak voltage generated by the voltage generator 516 for ablation in some embodiments is a square waveform with a peak-to-peak voltage in the range of 10 V to 2000 V, in some cases in the range of 100 V to 1800 V, in other cases in the range of about 28 V to 1200 V, and often in the range of about 100 V to 320V peak-to-peak.

The voltage and current generated by the voltage generator 516 may be delivered in a series of voltage pulses or AC voltage with a sufficiently high frequency (e.g., on the order of 5 kHz to 20 MHz) such that the voltage is effectively applied continuously (as compared with, e.g., lasers claiming small depths of necrosis, which are pulsed about 10 Hz to 20 Hz). In addition, the duty cycle (i.e., cumulative time in any one-second interval that energy is applied) of a square wave voltage produced by the voltage generator 516 is on the order of about 50% for some embodiments as compared with pulsed lasers which may have a duty cycle of about 0.0001%. Although square waves are generated and provided in some embodiments, the AC voltage signal is modifiable to include such features as voltage spikes in the leading or trailing edges of each half-cycle, or the AC voltage signal is modifiable to take particular shapes (e.g., sinusoidal, triangular).

The voltage generator 516 delivers average power levels ranging from several milliwatts to hundreds of watts per electrode, depending on the mode of ablation and state of the plasma proximate to the active electrode. The voltage generator 516 in combination with the processor 500 are configured to initially set the output energy of the voltage generator 516 (e.g., by controlling output voltage) based on the mode of ablation selected by the surgeon, and in some cases the setpoint within the particular mode of ablation. Moreover, while in a selected mode of ablation and setpoint within the mode of ablation, the processor 500 and/or voltage generator 516 may make control changes to compensate for changes caused by use of the wand. The control changes are discussed more below after a further discussion of the peristaltic pump 118. A description of various voltage generators 516 can be found in commonly assigned U.S. Pat. Nos. 6,142,992 and 6,235,020, the complete disclosure of both patents are incorporated herein by reference for all purposes. Reference is also made to commonly assigned U.S. Pat. No. 8,257,350, entitled "METHOD AND SYSTEM OF AN ELECTROSURGICAL CONTROLLER WITH WAVE-SHAPING", the complete disclosure of which is incorporated herein by reference as if reproduced in full below.

In some embodiments, the various modes of ablation implemented by the voltage generator 516 (along with the peristaltic pump 118) may be controlled by the processor 500 by way of digital-to-analog converter 506. For example, the processor 500 may control the output voltages by providing one or more variable voltages to the voltage generator 516, where the voltages provided by the digital-to-analog converter 506 are proportional to the voltages to be generated by the voltage generator 516. In other embodiments, the processor 500 may communicate with the voltage generator by way of one or more digital output signals from the digital output converter 508, or by way of packet-based communications using the communication device 512 (the communication-based embodiments not specifically shown so as not to unduly complicate FIG. 5).

Still referring to FIG. 5, in some embodiment the controller 104 further comprises a mechanism to sense the electrical current provided to the active electrode. In the illustrative case of FIG. 3, sensing current provided to the active electrode may be by way of a current sense transformer 532. In particular, current sense transformer 532 may have a conductor of the active terminal 518 threaded through the transformer such that the active terminal 518 becomes a single turn primary. Current flow in the single turn primary induces corresponding voltages and/or currents in the secondary. Thus, the illustrative current sense transformer 532 is coupled to the analog-to-digital converter 514 (as shown by the bubble A). In some cases, the current sense transformer may couple directly to the analog-to-digital converter 514, and in other cases additional circuitry may be imposed between the current sense transformer 532 and the analog-to-digital converter 514, such as amplification circuits and protection circuits. For example, in one example system the current sense transformer 532 is coupled to an integrated circuit device that takes the indication of current from the current sense transformer 532, calculates a root-mean-square (RMS) current value, and provides the RMS current values to the processor 500 through any suitable communication system (e.g., as an analog value applied the A/D 514, as a digital value applied to the multiple inputs of the D/I 510, as a packet message through the communication port 512). The current sense transformer is merely illustrative of any suitable mechanism to sense the current supplied to the active electrode, and other systems are possible. For example, a small resistor (e.g., 1 Ohm, 0.1 Ohm) may be placed in series with the active terminal 518, and the voltage drop induced across the resistor used as an indication of the electrical current.

Given that the voltage generator 516 is electrically floated, the mechanism to sense current is not limited to the just the active terminal 518. Thus, in yet still further embodiments, the mechanism to sense current may be implemented with respect to the return terminal 524. For example, illustrative current sense transformer 532 may be implemented on a conductor associated with the return terminal 524.

In some example systems, the feedback parameter used by the processor 500 regarding the voltage generator 516 is the electrical current flow. For example, in systems where the voltage generator can accurately produce an output voltage independent of the impedance of the attached load, the processor 500 having set point control for the voltage created by the voltage generator 516 may be sufficient (e.g., to calculate a value indicative of impedance of the electrode circuit and plasma proximate the active electrode). However, in other cases, voltage too may be a feedback parameter. Thus, in some cases the active terminal 518 may be electrically coupled to the analog-to-digital converter 514 (as shown by bubble B). However, additional circuitry may be imposed between the active terminal 518 and the analog-to-digital converter 514, for example various step-down transformers, protection circuits, and circuits to account for the electrically floated nature of the voltage generator 516. Such additional circuitry is not shown so as not to unduly complicate the figure. In yet still other cases, voltage sense circuitry may measure the voltage, and the measured voltage values may be provided other than by analog signal, such as by way of packet-based communications over the communication port 512 (not shown so as not to unduly complicate the drawing).

Still referring to FIG. 5 (and also FIG. 1), controller 104 in accordance with various embodiments further comprises the peristaltic pump 118. The peristaltic pump 118 may reside at least partially within the enclosure 122. The peristaltic pump comprises the rotor 124 mechanically coupled to a shaft of the electric motor 534. In some cases, and as illustrated, the rotor of the electric motor may couple directly to the rotor 124, but in other cases various gears, pulleys, and/or belts may reside between the electric motor 534 and the rotor 124. The electric motor 534 may take any suitable form, such as an AC motor, a DC motor, and/or a stepper-motor. To control speed of the shaft of the electric motor 534, and thus to control speed of the rotor 124 (and the volume flow rate at the wand), the electric motor 534 may be coupled to a motor speed control circuit 536. In the illustrative case of an AC motor, the motor speed control circuit 536 may control the voltage and frequency applied to the electric motor 534. In the case of a DC motor, the motor speed control circuit 536 may control the DC voltage applied to the electric motor 534. In the case of a stepper-motor, the motor speed control circuit 536 may control the current flowing to the poles of the motor, but the stepper-motor may have a sufficient number of poles, or is controlled in such a way, that the rotor 124 moves smoothly. Stated otherwise, the rotor 124 moves smoothly due to the high number of steps per turn.

The processor 500 couples to the motor speed control circuit 536, such as by way of the digital-to-analog converter 506 (as shown by bubble C). The processor 500 may be coupled in other ways as well, such as packet-based communication over the communication port 512. Thus, the processor 500, running a program, may read electrical current supplied on the active terminal 518, may read voltage supplied on the active terminal 518, and responsive thereto may make speed control changes (and thus volume flow rate changes) by sending speed commands to the motor speed control circuit 536. The motor speed control circuit 536, in turn, implements the speed control changes. Speed control changes may comprise changes in speed of the rotor 124 when desired, stopping the rotor 124 when desired, and in some modes of ablation temporarily reversing the rotor 124.

The specification now turns to a more detailed description of the various modes of ablation that may be implemented by the electrosurgical system. Each mode of ablation is illustratively named based on the aggressiveness of the ablation. However, all the illustratively identified tissue types may be ablated in each and every mode, and thus providing an indication of the type of tissue expected to be ablated in each mode shall not be read as a limitation of the applicability of any particular mode. Ablating tissue in a mode not specifically designed for the tissue may result in unwanted effects, such as discoloration or removal of too much of the target tissue or removal at a rate deemed too rapid. The available modes of ablation of the system thereby provide enhanced performance where the management of output energy in conjunction with control of aspiration flow rates creates surgical results in each mode that are tuned to the targeted tissue, the rate of aggressiveness, or type of surgical procedure.

In accordance with the various embodiments, the electrosurgical controller 100 implements at least two, and in some embodiments four, modes of ablation to modulate the flow rate dynamically in the vicinity of an active electrode in order to regulate the RF output energy: a "low mode" which may be used for treatment, ablation, and removal of portions of cartilage; a "medium mode" which may be used for treatment, ablation, and removal of meniscus; a "high mode" which may be used for aggressive treatment, ablation, and removal of tissue; and a "vacuum mode" for removal of loose, free floating and/or trapped tissue. Each illustrative mode of ablation may be characterized by a range of energies that may be applied to the active electrode (hereafter just "energy range") and a corresponding range of aspiration flows. During operation within a particular mode of ablation, the output energy provided by the voltage generator 516 and volume flow rate provided by the peristaltic pump 118 (FIG. 1) may change based on operational conditions at the distal end 108 of the wand, but such changes shall not obviate the status of being within a particular mode of ablation. The following table characterizes at a high level the four illustrative modes of ablation.

TABLE 1

| Low Mode | Medium Mode | High Mode | Vacuum Mode |
|---|---|---|---|
| Low output energy to active electrode. | Medium output energy to active | High output energy to active electrode. | Low to High output energy to active |

TABLE 1-continued

| Low Mode | Medium Mode | High Mode | Vacuum Mode |
|---|---|---|---|
| Low aspiration flow. | electrode. Medium aspiration flow. | High aspiration flow. | electrode. Very high or pulsed aspiration flow. |

Each mode will be discussed in turn.

The low mode is designed specifically for the treatment and selective ablation of articular cartilage or other very sensitive tissue. This low mode is particularly appropriate for chondroplasty and meniscus finishing or sculpting. However, cartilage does not re-grow, and thus the amount of cartilage ablated by a surgeon during a chondroplasty procedure is in most procedures very small. The primary concern of the surgeon may be to carefully remove diseased cartilage while at the same time reducing the damage to the underlying chondral tissue that remains. For these reasons, the illustrative low mode is characterized by low output energy provided to the active electrode, as well as low volume flow rate for the aspiration. In particular, in this mode of ablation output energy delivery during treatment is desired to increase cell viability and to create reduced instantaneous output energy dissipation and heat production in the vicinity of the treatment site. The reduced suction flow and low volume flow rate associated with this mode of operation may result in a plasma and electrode circuit having a higher overall impedance.

In the low mode of ablation, the processor 500, executing a program, controls the voltage generator 516 and peristaltic pump 118 to implement relatively high target impedance for the electrode circuit, and to avoid plasma collapse. In some embodiments, the controller 104 may provide predetermined output energy, and for impedance values falling within a predetermined range, the controller 104 may control impedance based solely on changes in speed of the peristaltic pump 118. For variations in impedance that fall outside with a predetermined range, the control strategy may also rely on changes in output energy supplied by the voltage generator 516. For example, control action in response to decreasing impedance (as calculated based on the current and/or voltage applied to the active electrode) may involve slowing, stopping, or temporarily reversing the peristaltic pump 118 (FIG. 1), and in some systems increasing the output energy supplied by the voltage generator 516. In some embodiments, changes in the electrical output energy produced by the voltage generator 516 may be implemented more quickly than changes in peristaltic pump 118 speed, and thus in some embodiments an initial reaction to measured decreasing electrode circuit impedance may be momentarily increasing the level of supplied output energy, followed by decreasing pump speed and lowering again the supplied output energy.

The medium mode of operation is designed specifically for ablation of fibro-cartilaginous tissue like meniscal tissue, but other types of tissue may also be ablated in the medium mode. This medium mode may also be appropriate for the electrosurgical treatment of labrum tissue. When ablating meniscus, the surgeon may be interested in ablating more tissue volume than with respect to cartilage, but browning of the remaining meniscus is disfavored. For at least this reason, the illustrative medium mode is characterized by medium output energy provided to the active electrode, as well as medium volume flow rate of the aspiration in order to preserve tissue consistency. In particular, in this mode of ablation output energy delivery during treatment is desired to increase tissue matrix preservation and to reduce tissue matrix alteration with reduced or no tissue discoloration, or cross-linking of the collagen fibers that could result in mechanical alterations. The medium volume flow rate may result in the electrode circuit having a lower impedance than the low mode.

In the medium mode of ablation, the processor 500, executing a program, controls the voltage generator 516 and peristaltic pump 118 (FIG. 1) to implement a medium target impedance for the electrode circuit. In some embodiments, the controller 104 may provide predetermined output energy, and for impedance values falling within a predetermined range, the controller 104 may control impedance based by changing speed of the peristaltic pump 118. For variations in impedance that fall outside of a predetermined range, the control strategy may also rely on changes in output energy supplied by the voltage generator 516. For example, control action in response to decreasing impedance (as calculated based on the current and/or voltage applied to the active electrode) may involve slowing and/or stopping the peristaltic pump 118, and in some systems increasing the output energy supplied by the voltage generator 516. In some embodiments, changes in the electrical output energy produced by the voltage generator 516 may be implemented more quickly than changes in peristaltic pump 118 speed, and thus in some embodiments an initial reaction to measured decreasing electrode circuit impedance may be momentarily increasing the level of supplied output energy, followed by decreasing pump speed and lowering again the supplied output energy.

The illustrative high mode of ablation is designed specifically for quickly removing tissue. By way of example, the high mode may be used for sub-acromial decompression treatments or ACL stump debridement. For this reason, the illustrative high mode is characterized by high output energy provided to the active electrode, as well as high volume flow rate for aspiration. In particular, in this mode of ablation output energy delivery during treatment is adjusted for increased tissue removal with continuous aspiration flow volume to pull tissue closer to the wand for more efficient ablation rates. The high volume flow rate will result in having lower electrode circuit impedance, and regular (but uncontrolled) plasma collapse. Thus, plasma collapse is expected in the high mode based on the aggressive aspiration flow, but the high mode may implement a minimum volume flow rate, and thus a minimum peristaltic pump speed, even if such minimum speed results in plasma collapse. The plasma should be reinstated as tissue contact ensues.

In the high mode of operation, the processor 500, executing a program, controls the voltage generator 516 and peristaltic pump 118 to implement low target impedance for the electrode circuit. In some embodiments, the controller 104 may provide predetermined output energy, and for impedance values falling within a predetermined range, the controller 104 may control impedance based on changes in speed of the peristaltic pump 118. For variations in impedance that fall outside with a predetermined range, the control strategy may also rely on changes in output energy supplied by the voltage generator 516. For example, control action in response to decreasing impedance (as calculated based on the current and/or voltage applied to the active electrode) may involve slowing the peristaltic pump 118, but only to predetermined minimum volume flow rate.

The illustrative vacuum mode of ablation is designed specifically for quickly removing loose tissue and tissue fragments within the surgical field. For this reason, the illustrative vacuum mode is characterized by variable output energy provided to the active electrode, as well as the highest volume flow rate as between the various modes (when the aspiration is active). In particular, in this mode of ablation output energy delivery during treatment is desired to be optimized for fast digestion of debris within the surgical field in conjunction with a high volume flow rate in order to attract debris to the wand tip. The high volume flow rate will result in lower electrode circuit impedance. When tissue debris is in contact with the electrode, the flow is lessened to better digest the tissue. When the electrode has no tissue in its proximity, the voltage is dropped to lessen electrode wear.

Figure 6:
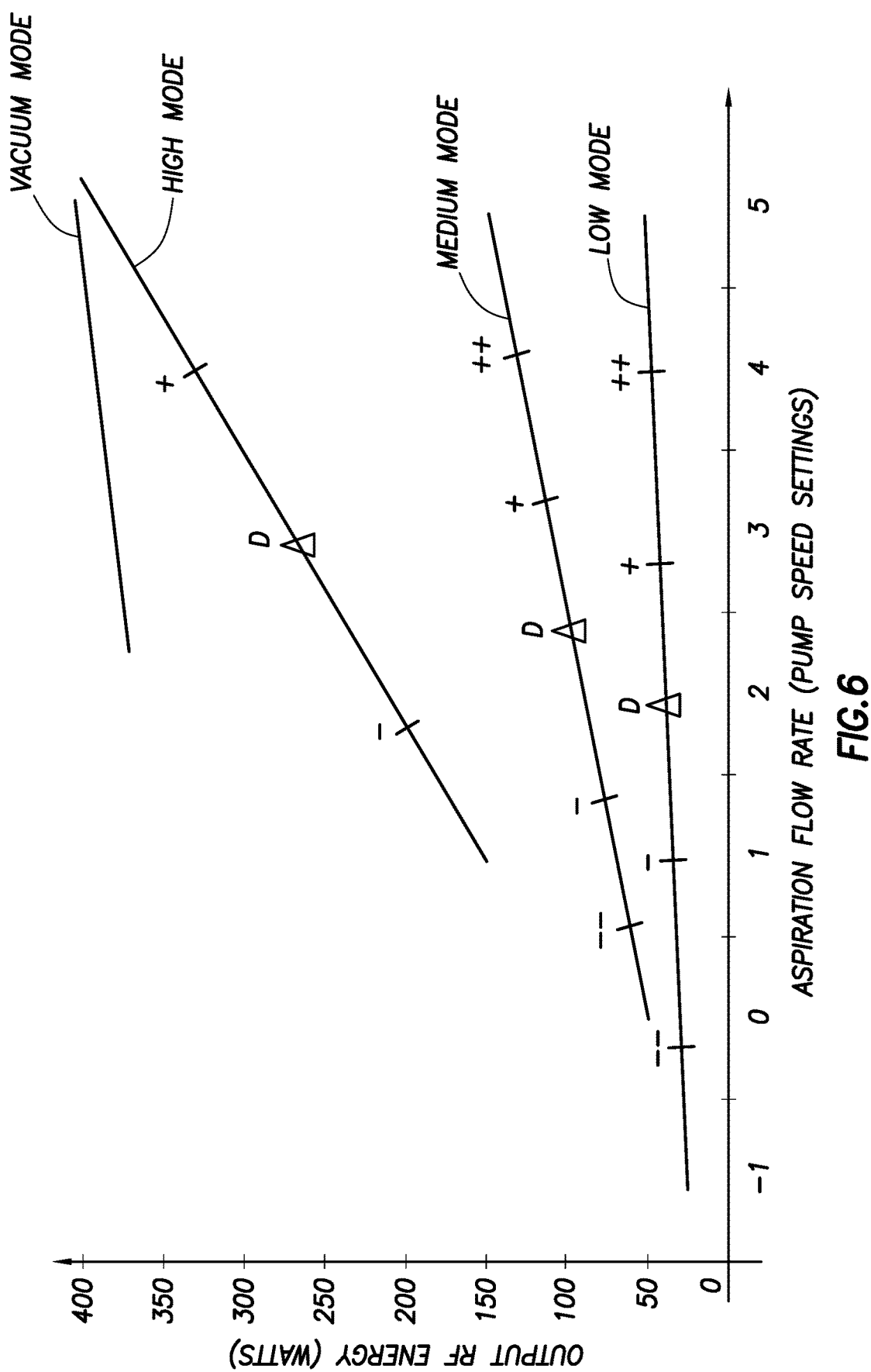
FIG. 6 shows an example graph relating output RF energy and aspiration flow of various modes, including setpoints within each mode, in accordance with at least some embodiments.

FIG. 6 shows a graph that relates possible energy ranges (output RF energy) to aspiration flow rate (shown as pump speed settings) for four example modes of ablation—low mode, medium mode, high mode, and vacuum mode. In particular, for each mode of ablation the electrosurgical controller 104 is programmed to operate within an energy range of output RF energy and a range of aspiration flow rates. For example, in the "low mode" of ablation described above controller 104 may be pre-programmed to operate within an energy range from 25-50 Watts, and aspiration flow range from an example "−1" (i.e., reverse motor direction) to "5", which in some cases may result in an aspiration flow in a range from 0-45 ml/min. For the example "medium mode" of ablation, described above, controller 104 may be pre-programmed to operate within an energy range from 50-150 Watts, and aspiration flow range from an example "0" (i.e., peristaltic motor stopped) to "5". For the example "high mode" of ablation described above, controller 104 may be pre-programmed to operate within an energy range from 150-400 Watts, and aspiration flow range from an example "1" to "5". For the example "vacuum mode" of ablation described above, controller 104 may be pre-programmed to operate within an energy range from 350-400 Watts, and aspiration flow range from an example "2" to "5". These example output energy and flow rates and energy ranges are merely examples, and could vary in actual values.

Moreover, FIG. 6 illustrates that, within at least some of the modes of ablation, differing energy setpoints are contemplated. That is, in some example systems, within the pre-programmed energy ranges, the processor 500 (executing a program) implements at least three, and in some cases five, energy setpoint levels within a mode of ablation to enable changes of both the output RF energy (and correspondingly the flow rate in the vicinity of an active electrode). For example, FIG. 6 illustrates that each of the low mode, medium mode, and high mode may have an initial or default energy setpoint and a corresponding default aspiration volume flow setpoint (labeled in each mode with a "D" and triangular symbol). In FIG. 6, the default energy setpoints are shown to reside in the middle of the energy range, but in other cases the default energy setpoints may be at the lower or upper ends of the respective energy ranges.

Considering the low mode as representative of modes of ablation having multiple energy setpoints within the energy range, two energy setpoints with energies above the default energy setpoint may be implemented, and these higher energy setpoints are designated in FIG. 6 as the (+) and (++) energy setpoints. By way of manually activating a control input (e.g., foot pedal, button on the controller, graphical user interface such as a touch screen, or a button on the wand), the surgeon may increase the setpoint energy level to the plus (+) or (++) level performance. Likewise, two energy setpoints with energies below the default energy setpoint may be implemented, and these lower energy setpoints are designed in FIG. 6 as the (−) and (−−) energy setpoints. By way of manually activating a control input (e.g., foot pedal, button on the controller, or a button on the wand), the surgeon may decrease the setpoint energy level to the minus (−) or (−−) level performance. Any number of energy setpoints within a mode of ablation may be implemented. While the low mode and medium mode in FIG. 6 each have five energy setpoints, the high mode is illustrative shown to have only three energy setpoints within the energy range—a default energy setpoint, a plus (+) level and a minus (−) level. It is likewise possible for the vacuum mode to have varying energy setpoints, but no such energy setpoints are illustrated in FIG. 6 to exemplify that in some systems not all modes have multiple energy setpoints within their respective energy ranges.

By way of example, in the previously described "high mode" the default (D) energy setpoint may be about 250 Watts, and an aspiration flow setpoint of level 3 (which, for example, may result in an aspiration flow rate of 200 ml/min). By advancing the controller 104 operational parameter to the plus (+) setpoint due to either a desired increase in output energy or aspiration flow rate, the controller 104 then increases each performance characteristic in a complementary fashion, such as by adjusting the output energy to about 325 Watts and the aspiration flow setpoint to level 4 (which, for example, may result in an aspiration flow rate of 300 ml/min). Alternatively, a user may desire a decrease in both output energy and flow rate setpoint, and may accordingly choose to set back the energy setpoint to the minus (−) level performance and flow rate setpoint. Thus, each mode of operation may have a plurality of performance levels delineated by energy setpoints and flow setpoints, yet operation of any of the plurality of performance levels shall still be considered to be within a particular mode of ablation.

Figure 7:
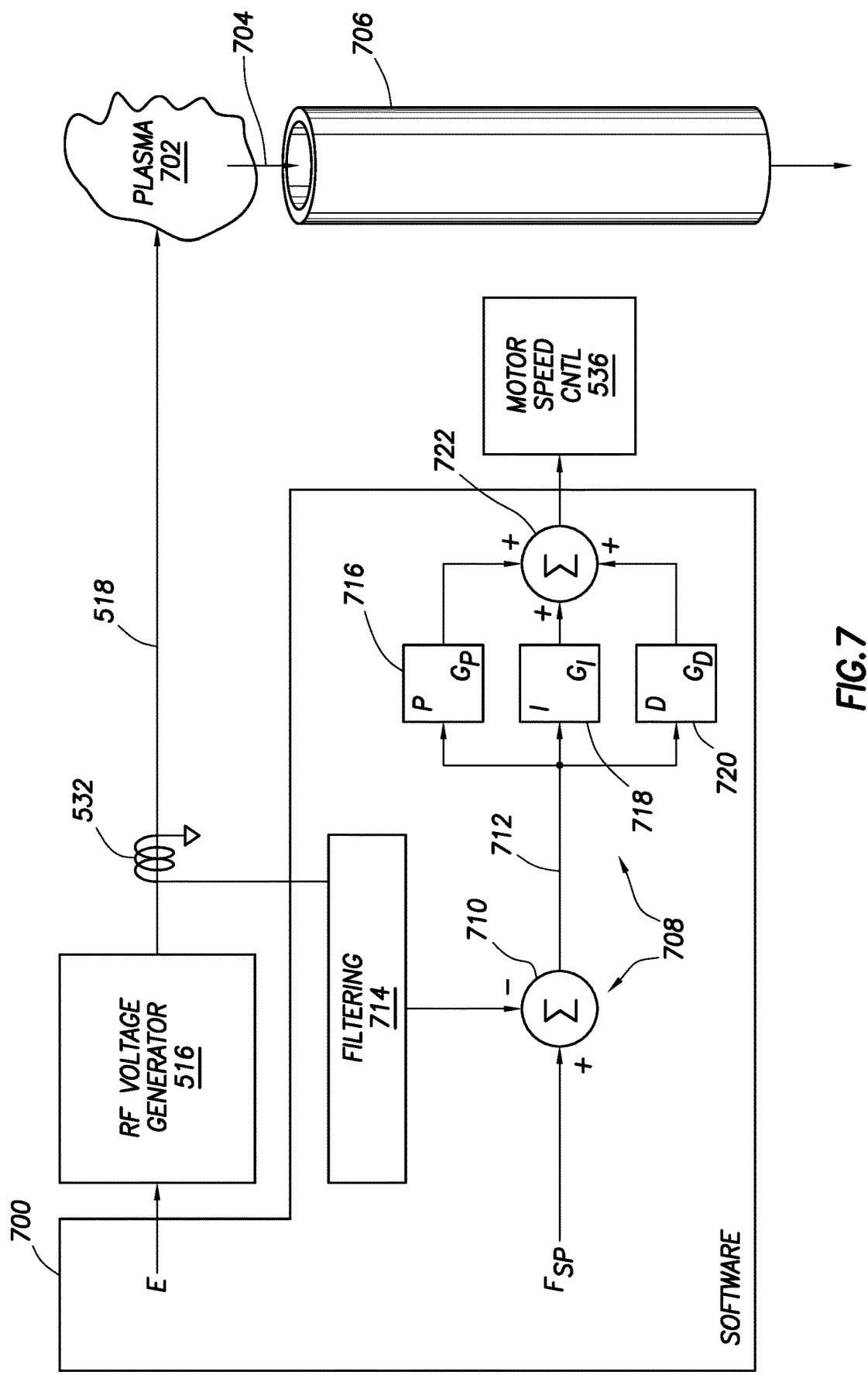
FIG. 7 shows, in block diagram form, various control algorithms in accordance with at least some embodiments.

The specification now turns to implementation of the control loops within controller 104. In accordance with example systems, the control loops are implemented as software by the processor 500, but in other embodiments portions or all the control loops may be implemented in discrete logic. FIG. 7 shows, in block diagram form, the logical interaction of the control loops, as well as interaction between software executed by the processor and various components of the controller 104. In particular, FIG. 7 shows software as the various components within the software block 700, and likewise shows the voltage generator 516, the motor speed control 536, the active terminal 518, and current sense transformer 532. Other components of the controller 104 are omitted so as not to unduly complicate the figure. Moreover, FIG. 7 also illustrates a plasma 702 in operational relationship to aspiration flow through an aperture (shown by arrow 704 in relation to tube 706).

In accordance with example systems, the software 700 generates or selects an energy value (shown as E in the figure) as well as a flow setpoint (shown as Fsp in the figure). The energy value E and flow setpoint Fsp are generated or selected based the mode of ablation chosen by the surgeon (and the energy setpoints within the mode of ablation). The example energy value E may be applied to the voltage generator 516 in any suitable manner, such as those discussed above. In example systems, the energy value E is a single value representing the desired output energy, but in other cases the energy value E may be a value indicative of voltage to be created by the voltage generator 516, or a combination of values representing a desired voltage or electrical current to be created by the voltage generator 516. Based on the energy setpoint Esp, the voltage generator 516 may produce the desired voltage on the active terminal 518, ultimately creating plasma 702. During periods of time when voltage is being supplied by the voltage generator 516, the electrical current may be measured by the current transformer 532, and an indication of the instantaneous electrical current may be supplied to the software 700 as indicated in the FIG. 7.

In accordance with example systems, during the low mode, medium mode, high mode, and certain periods of time in the vacuum mode, the software 700 implements closed-loop control. More particularly, the example system may apply the flow setpoint Fsp to a proportional-integral-differential (PID) control loop 708. In example systems, the flow setpoint Fsp is a single value representing the desired volume flow of fluid, but in other cases (and for ease in coding the control loops) the flow setpoint Fsp may be a value indicative of electrical current since electrical current provided by the voltage generator and volume flow of fluid are directly proportional during periods of time when plasma is present. In the example logical control-loop flow, the flow setpoint Fsp may be applied to summation block 710. The summation block 710 may create an error signal 712 by subtracting the feedback parameter (in this illustrative case, the electrical current measured by the current transformer 532, FIG. 5) from the flow setpoint Fsp. As illustrated, the feedback parameter may be subjected to various filtering operations in filter block 714, and such filtering is discussed in greater detail below. The error signal 712 may be applied to a proportional block 716, an integral block 718, and a differential block 720. Each block may be associated with gain value: $G_P$ for the proportional block 716; $G_I$ for the integral block 718; and $G_D$ for the differential block 720. Each example block 716, 718, and 720 produces a response signal, and the respective response signals are summed at summation block 722. The summed signal is then converted to a proper format for the motor speed controller 536 and applied to the motor speed controller 536 to control peristaltic pump 118 speed. Not all the PID blocks 716, 718, and 720 need be implemented simultaneously. In some cases only proportional-integral (PI) control may suffice, and thus the differential block 720 may be omitted or disabled (e.g., by setting the gain $G_D$ to zero).

The specification now turns to an explanation of PID control loop 708 control in the low mode, medium mode, high mode, and certain periods of time during the vacuum mode. First, consider that the controller 107, plasma 702, and volume flow of fluid 704 have reached a steady state point that matches the various setpoints, and that the RF voltage generator 516 is cable of providing a substantially constant voltage regardless of impedance. Then considerer that, perhaps based on movement of the active electrode of the wand against tissue, the electrode circuit impedance increases. Increasing impedance results in decreasing electrical current flow. Responsive to the decreasing electrical current flow the summation block 710 creates an increasing magnitude error signal 712 that is applied to various blocks 716, 718, and 720. The end result of this example situation is an increasing flow of fluid drawn into the aperture (by increasing the peristaltic pump speed) responsive to the electrosurgical controller detecting the active electrode is in operational relationship with tissue.

Now consider again that the controller 107, plasma 702, and volume flow of fluid 704 have reached a steady state point that matches the various setpoints, and that the RF voltage generator 516 is capable of providing a substantially constant voltage regardless of impedance. Then considerer that, perhaps based on of movement of the active electrode of the wand away from tissue, the electrode circuit impedance decreases. Decreasing impedance results in increasing electrical current flow. Responsive to the increasing electrical current flow the summation block 710 creates a decreasing magnitude error signal 712 that is applied to various blocks 716, 718, and 720. The end result of this example situation is a decreasing flow of fluid drawn into the aperture (by decreasing the peristaltic pump speed) responsive to the electrosurgical controller detecting the active electrode has moved away from tissue. The specification now turns to distinguishing the various modes of ablation.

The various modes of ablation are distinguishable based not only on the output energy and flow ranges discussed above (and specific setpoints within the respective ranges), but also based on the gain setpoints implemented. For example, the low mode of ablation may implement a first set of gain values $G_{PL}$, $G_{IL}$, and $G_{DL}$, and the high mode of ablation may implement a second set of gain values $G_{PH}$, $G_{IH}$, and $G_{DH}$ that are distinct from the low mode of ablation. Moreover, in systems that implement different output energy and flow setpoints within a mode of ablation, each energy setpoint may have a set of gain values. For example, the low mode of ablation may implement a first set of gain values at the default energy setpoint $G_{PLD}$, $G_{ILD}$, and $G_{DLD}$, and the low mode of ablation may implement a second set of gain values at the (+) energy setpoint $G_{PL+}$, $G_{IL+}$, and $G_{DL+}$, and so forth.

Moreover, other parameters may be associated with the PID control loop 708 that are not specifically delineated in FIG. 7. For example, the integral block 718 may have additional parameters in the form of reset time for the integration, or maximum allowed values of the integral block 718 response. Such additional parameters may reduce or prevent "wind up" of the response of the integral block 718 in certain situations (such as extended periods of plasma collapse or significant voltage generator pulsing). Further still, the range of motor speed control is different between the example modes of ablation, with some modes (e.g., the low mode) having the ability to stop and even reverse direction of the peristaltic pump, and with other modes implementing minimum non-zero speeds for the peristaltic pump (e.g., the high mode), and thus the summation block 722 may have additional parameter which limit the range of values that can be applied to the motor speed controller 536 regardless of the actual summation of the various inputs.

In some example systems, gain scheduling may be implemented by the PID control loop 708 (FIG. 7). That is, in some systems within a particular mode of ablation different gains may be used as a function of the magnitude of the error signal 712. Consider as an example of gain scheduling the proportional block 716. In systems where gain scheduling based on the magnitude of the error signal 712 is used, when the magnitude of the error signal 712 exceeds a first predetermined threshold, a first gain value $G_{P1}$ may be used by the proportional block 716, and when the magnitude of the error signal 712 exceeds a second higher predetermined threshold, a second gain value $G_{P2}$ may be used by the proportional block 716 where the second gain value is different than the first gain value. Each example block 716, 718, and 720 may use gain scheduling within a particular mode of ablation, and different gain schedules may be used based on the setpoints within each mode of ablation (i.e., a first gain schedule for the default mode, and different gain schedule for each of the (+), (++), (−), and (−−) setpoints. Moreover, gain scheduling may be used within some or all of the modes of ablation. For example, the gain value for the proportional block 716 for the low mode of ablation $G_{PL}$ may be a set of values, such that $G_{PL}=\{G_{PL1}, G_{PL2}, G_{PL3}\}$. As another example, the gain value for the proportional block 716 for the high mode of ablation $G_{PH}$ may be a set of values, such that $G_{PH}=\{G_{PH1}, G_{PH2}, G_{PH3}\}$. Further still, as the electrode wears due to use (discussed more below), the gains setpoints, and gain schedules, may be changed.

In some example systems, the controller 104 is pre-programmed with all the various parameters used to identify and implement the modes of ablation. For example, the ROM 504 of the controller 104 may be pre-programmed with the some or all of the various parameters used to identify and implement the modes of ablation, and the software 700 (also stored on the ROM 504) may, when executed, read the parameters and implement the modes of ablation based on the parameters. In other systems, however, the various parameters used to identify and implement the modes of ablation may be dependent on the wand 102 (e.g., the exposed surface area of the electrode 202). Thus, the values associated with each mode of ablation may be wand 102 dependent, and again the controller 104 may be pre-programmed with some or all the various parameters for each wand 102 which may be used with the controller 104. In such systems, the wand 102 may be identified by the controller by any suitable means (e.g., identified by the surgeon selecting the wand from a list of supported wands using the display 130 and buttons 132, or the wand may be identified electrically by the controller based on information readable by the pins in the connector 114). In yet still further cases, different sets of parameters may be used with the same wand to implement different characteristics of the modes of ablation.

Still referring to FIG. 7, the discussion now turns to example filtering performed in the filtering block 714. In particular, while a value indicative of the electrical current read by the current transformer 532 may be logically applied directly to the summation block 710, in some example systems the overall control of the plasma 702 may be better controlled by implementing filtering within the filtering block 714. In order to logically tie the example filtering scenarios to the plasma control, a brief description of operational phenomenon associated with the voltage generator 516 and plasma 702 is in order. The first operational phenomenon is plasma 702 "collapse" (i.e., the plasma is extinguished). Plasma collapse is more likely in some operational situations, such as in the modes of ablation implementing higher volume flow of fluid. During periods of time when the plasma has collapsed, electrical current may flow through fluids and/or tissue abutting the electrode 202 of the wand in a thermal mode, and in the impedance to electrical current flow in the thermal mode is lower than the impedance of plasma. In most cases, the plasma is quickly re-established. Thus, plasma collapse may result in a high frequency electrical current "spike". The second operational phenomenon is voltage generator 516 "pulsing". Pulsing of the voltage generator 516 is a temporary cessation of voltage and current flow to the electrode 202 based on the output energy delivery meeting or exceeding a predetermined output energy threshold. For example, in some systems the voltage generator 516 may temporarily cease providing a voltage (and therefore cease providing a current) when the output energy delivery meets or exceeds 400 Joules per second. When output energy delivery is stopped, the plasma is extinguished, electrical current drops (e.g., to zero). When output energy is again provided the system progresses through a thermal mode (in which a current spike is seen) and then to a plasma mode.

Figure 8:
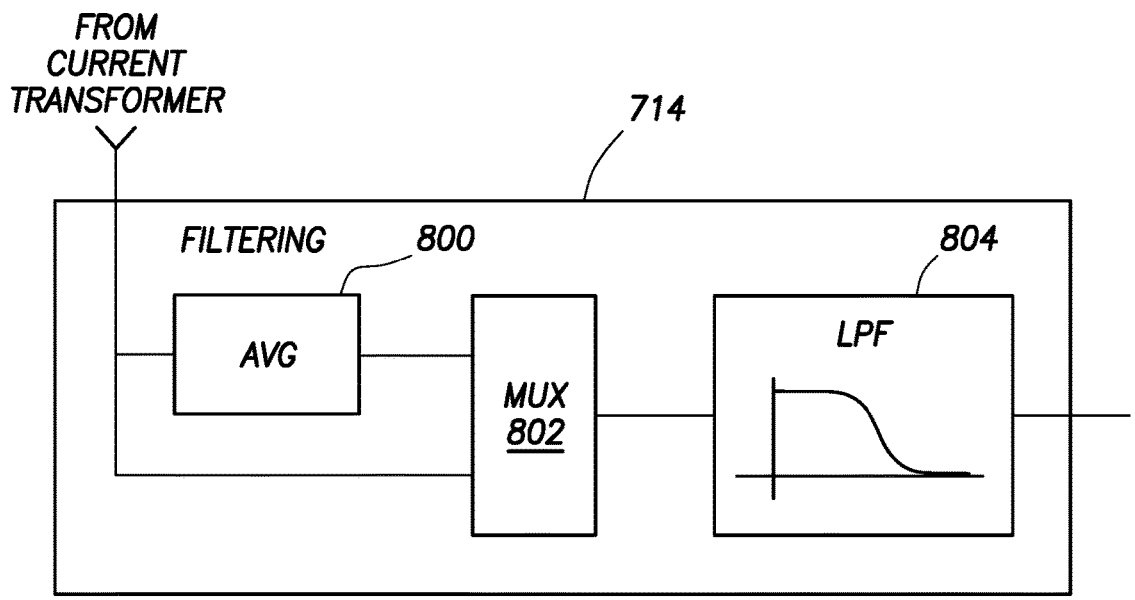
FIG. 8 shows, in block diagram form, filter algorithms in accordance with at least some embodiments.

Volume flow of fluid provided during periods of plasma collapse and generator pulsing has little effect on re-establishing the plasma, and thus in some example systems no (or very little) control action in regard to the volume flow of fluid may be taken responsive to the plasma collapse and generator pulsing events. Thus, in accordance with example systems the filtering block 714 implements control strategies to deal with plasma collapse and generator pulsing. FIG. 8 shows, in block diagram form, one example control strategy logically implemented with the filtering block 714. In particular, the feedback parameter in the form of an indication of electrical current being supplied by the generator is applied to an averaging block 800. As the name implies, the averaging block 800 creates a running average value of the indication of electrical current during periods of time when plasma is present (e.g., over the last 500 milli-seconds, or the last second). The running average value, as well as the indication of electrical current being supplied, is applied to a multiplexer 802. During periods of time of generator pulsing, the multiplexer 802 passes the running average value to downstream logical components. That is, PID control loop 708 is provided the running average value created by the averaging block 800, rather than the instantaneous indication of electrical current being supplied, during periods of generator pulsing. In this way, the PID control loop 708 may take little or no action responsive to the generator pulsing. When the generator pulsing event is completed, and plasma is re-established, the multiplexer 802 again provides the instantaneous indication of electrical current being supplied to the downstream logical components. Thus, the averaging block 800 and multiplexer 802 may be considered to address pulsing issues; however, other logical mechanism may be equivalently used.

The indication of electrical current flow propagating from the multiplexer 802 may then be applied to a low-pass filter block 804. As the name implies, the low-pass-filter block 804 filters the signal to remove high frequency components, such as current spikes associated with plasma collapse. Thus, PID control loop 708 is provided a low-pass filtered version of the indication of electrical current created by the low-pass filter block 804. In this way, the PID control loop 708 may take little or no action responsive to plasma collapse. Thus, the low-pass filter block 804 may be considered to address the plasma collapse issue; however, other logical mechanism may be equivalently used.

The specification now turns to control in the vacuum mode of ablation in accordance with example systems. In the vacuum mode of ablation, during periods of time when the active electrode 202 is not in operational relationship with tissue (as determined based on low overall impedance), a relatively high volume flow of fluid is drawn into the aperture. However, when the active electrode encounters tissue (as determined based on increasing impedance), rather than increase the volume flow of fluid, in the vacuum mode the opposite control strategy is implemented. That is, when the active electrode encounters tissue (and the impedance increases), the volume flow of fluid drawn into the aperture decreases. The theoretical basis for the control strategy is that the vacuum mode is designed for quickly removing free floating and/or loosely held tissue, but where the volume density of the tissue is low. Thus, there may be large volumes of bodily fluids or saline containing no tissue drawn into the aperture. The volume flow of fluid is high during periods of time when no tissue is present near the active electrode, but the volume flow of fluid slows during periods of time when tissue is in operational relationship with the active electrode to enable increased digestion rate of tissue and more thorough molecular dissociation and reduction of the tissue to decrease clogging. In some cases, during periods of time when tissue is in operational relationship with the active electrode, the volume flow of fluid may be controlled in a fashion similar to the other modes of ablation. In yet still other cases, the lack of tissue may be sensed by pulsing of the generator.

Returning briefly to FIG. 7, in some example systems the volume flow of fluid during the vacuum mode is based on the PID control loop 708 standing alone, in combination with a change in flow setpoint Fsp. That is, during periods of time when no tissue is in operational relationship with the active electrode, the flow setpoint Fsp in the vacuum mode may be set very high; however, when tissue is in operational relationship with the active electrode, the flow setpoint Fsp is reduced to implement the decrease in the volume flow of fluid. Moreover, the various gains associated with the blocks 716, 718, and 720 may be changed simultaneously with changing the flow setpoint Fsp responsive to the controller detecting the active electrode is in operational relationship with the tissue. However, other control strategies are possible, such as discussed with respect to FIG. 9.

Figure 9:
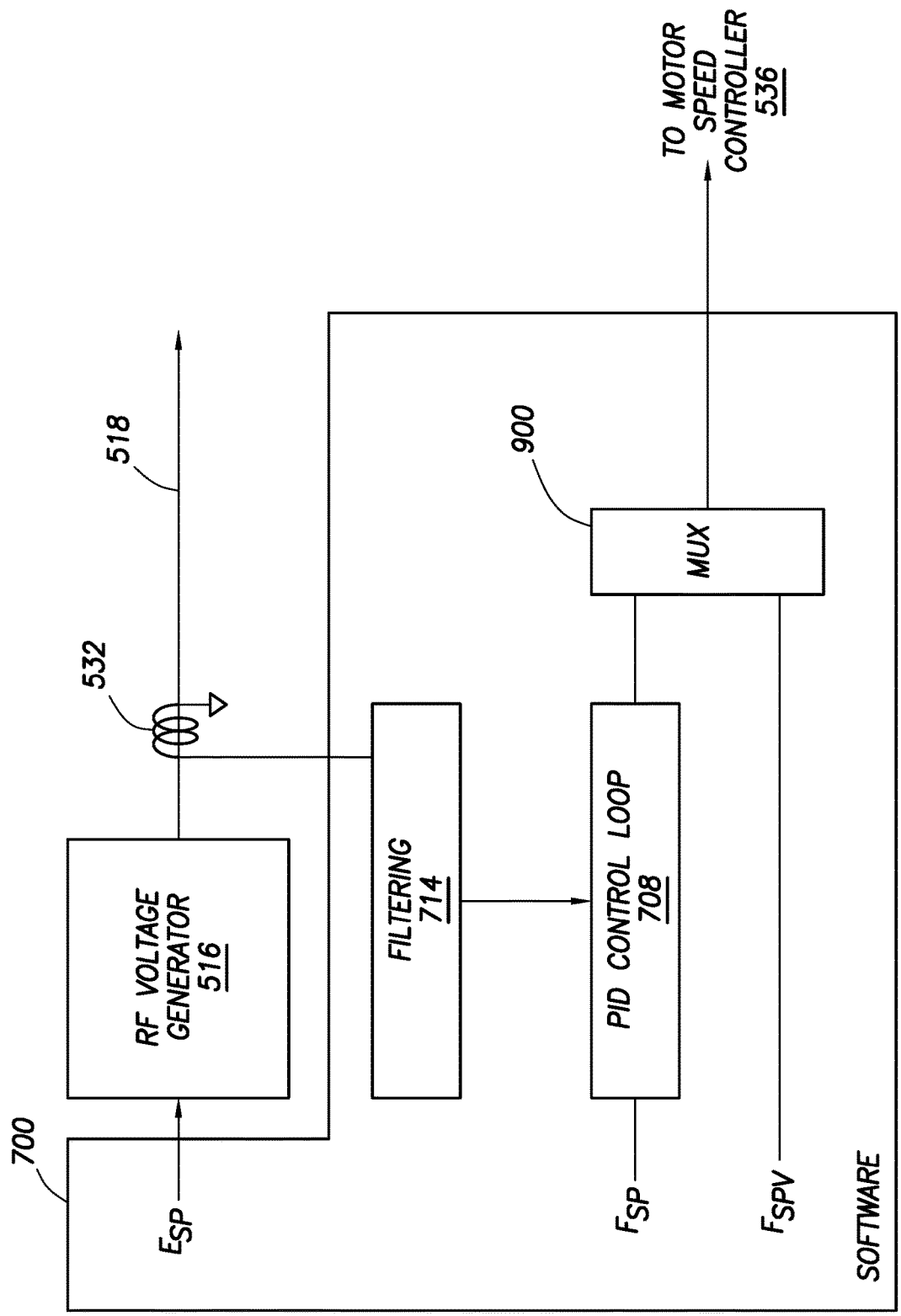
FIG. 9 shows, in block diagram form, various control algorithms in accordance with at least some embodiments.

FIG. 9 shows, in block diagram form, a logical interaction of the control strategies in the vacuum mode, as well as interaction between software executed by the processor and various components of the controller 104. In particular, FIG. 9 shows software as the various components within the software block 700, and likewise shows the voltage generator 516, the motor speed control 536, the active terminal 518, and current sense transformer 532. Other components of the controller 104 are omitted so as not to unduly complicate the figure. During periods of time when plasma is being maintained by an active electrode of a wand in the vacuum mode, but where no tissue is in operational relationship to the active electrode, the flow setpoint Fspv may be directly applied to the motor speed controller 536 though logical multiplexer 900. As shown, the speed is set, in many cases predetermined, and no changes are made the based on any feedback parameter. Thus, during the period of time when no tissue is in operational relationship with the active electrode, the example system implements open-loop flow control. However, when the system determines that there is tissue in operational relationship to the active electrode. The multiplexer 900 may be operated to couple the control signal derived from the PID control loop 708 to the motor speed controller 536. Given that the flow setpoint Fspv is higher than the flow setpoint Fsp in this situation, the flow of fluid into the aperture decreases, and then closed-loop flow control is exercised responsive to the electrosurgical controller detecting the active electrode is in operational relationship with tissue.

Simultaneously with implementing the various control strategies for the modes of ablation, the controller 104 may also perform clog detection. That is, in some situations a large piece of tissue may enter the aperture 404 behind the active electrode 400 causing a clog either at the location of the aperture, or at another location within the wand and/or tubing. A clog reduces or stops the volume flow of fluids into the aperture. In accordance with the various embodiments, the presence of a clog may be detected by the processor 500 (executing a program) indirectly based on other parameters. For example, when a clog is present the impedance of the electrode circuit changes and thus electrical current flow changes and becomes stable (in relation to the non-clog condition). Moreover, when a clog is present the fluids within the flexible tubular member 116 may pool and/or become stationary and thus cause localized temperature increases. Further still, peristaltic pump 118 speed is related to impedance changes (assuming corresponding flow of fluid), but in the presence of a clog changes in peristaltic pump speed have little or no effect on impedance. The stator movement can be sensed, for example, by Hall Effect Sensors. These sensors show that the stator up and down movement is a predictable cycle in normal operation. When there is a clog, the cycle of movement is dampened and the clog may be detected.

Thus, in accordance with the example embodiment the controller 104 (more particularly the processor 500 executing a program) determines the presence of a clog based on two or more of the above-noted parameters. For example, the processor 500 may make an initial determination of a clog based on an impedance change and then stabilization, and the clog determination may be verified by implementing control changes in volume flow of fluid that have no effect on impedance. As yet another example, the processor 500 may make an initial determination of a clog based on an impedance change and then stabilization, and the clog determination may be verified by reading increasing temperature of the fluid flow in the tubular member 116 (such are read by temperature measurement device 304 of FIG. 3). Other variations are possible. For example, the initial determination may be based on reading increasing temperature, and the verification based on either impedance changes and/or lack of control effect. Additionally, pressure variations or oscillations of the fluid within tubular member 116 may be sensed in the form of tubing wall pulsing, causing the flexible tubular member 116 to variably expand and contract. Inasmuch as impedance and electrical current are related (for a constant or known applied voltage), changes in impedance and changes in electrical current may be interchangeable in the determinations and/or verifications. Any suitable measure of change of impedance (or electrical current) may be used, such as variations, changes in standard deviation. The specification now turns to electrode wear considerations.

The active electrode of the example wand 102 is the location about which plasma is formed. The plasma not only ablates various tissues, but the plasma also etches the active electrode, thus removing metallic material over time. Etching of the active electrode reduces the size and/or exposed surface area of the active electrode, and also reduces the "sharpness" of asperities (if present) defined by the active electrode. After continued use, the active electrode may be reduced in size to the point that the therapeutic benefit is reduced or eliminated—that is, used beyond useful life. If used beyond the useful life, the active electrode may fail, such as by cracking, splitting, or even becoming detached from the distal tip 108, thus lodging itself inside the body at the treatment site. Failure of the active electrode may result in serious complications, and thus should be avoided.

The amount of plasma time to which an active electrode may be exposed before failure varies based on the mode of ablation and the specifics of the wand 102. Modes of ablation using higher energies result in more aggressive etching of the active electrode, while modes of ablation using lower energies result in less aggressive etching. For example, the inventors of the current specification estimate that the example wand 102 discussed with respect to FIGS. 2-4 may have a useful life of 8 minutes if used exclusively in the high mode of ablation and have a useful life as long as 30 minutes is used exclusively in the low mode of ablation. It is contemplated that a surgeon will vary the modes during any particular electrosurgical procedures, and thus the useful life will be dependent upon the amount of time spent in each mode of ablation. In the example, the useful life may fall somewhere between 8 and 30 minutes.

In order to gauge the state of the active electrode, in accordance with example embodiments the electrosurgical controller 104 is designed and constructed to measure an indication of active electrode wear. In one example embodiment, the measurement is made just prior to each plasma activation. In particular, in one embodiment the controller 104 (and more particularly, software executed by the processor 500), receiving a command to create the plasma but prior to commanding providing output energy sufficient to create a plasma, commands the voltage generator to apply a test voltage to the wand circuit (e.g., terminal 518, conductors in the multiconductor cable 112, the active electrode 400, the return electrode, conductive fluids and other fluids/tissue between the active electrode and the return electrode, etc.). The test voltage is low enough that plasma is not created, but high enough to induce an electrical current flow through the wand circuit. The controller 104 measures the electrical current flow (e.g., by way of current transformer 532), and based on the voltage and current calculates an impedance of the wand circuit. The impedance of the fixed components, such as terminals, wiring, and even the conductive fluids, is known or calculable in advance. However, a portion of the overall impedance associated with the active electrode is dependent upon the remaining size of the active electrode and/or the remaining exposed surface area. Thus, the impedance of the active electrode can be measured. Once the active electrode impedance has been measured (and assuming the impedance value is above a predetermined threshold), the controller 104 may command the voltage generator 516 to increase the voltage to create the plasma. On the other hand, if the active electrode impedance indicates the active electrode is beyond its useful life, the controller 104 may refrain from providing sufficient voltage to create the plasma, and provide an alarm or alert (e.g., posting a message on display device 130).

In one example system, during periods of time when the impedance of the electrode circuit is being measured, the controller may apply a voltage in the range of 5-20 Volts. In some cases, the voltage is an alternating current (AC) voltage, and thus the 5-20 Volts may be a peak or RMS value. In other cases, the voltage applied may be a direct current (DC) voltage, in which case the indication of active electrode wear includes only a purely resistive component. In one example situation, a wand 102 having an active electrode that has not previously been exposed to plasma may have a real component of the measured impedance in the range of 40-100 Ohms. After the active electrode has been used to the point of being beyond useful life, the same active electrode may have a real part of the impedance of 200 Ohms or above.

In accordance with yet still further embodiments, the controller 104 may also calculate or estimate the remaining useful life of the active electrode. In particular, during of time when the voltage generator is providing output energy sufficient to establish plasma proximate to the active electrode, the controller 104 may calculate or estimate the remaining useful life of the active electrode based on the current mode of ablation (e.g., based on the current energy level being provided). The controller may provide an indication of the remaining useful life to the surgeon, such as by displaying the estimated remaining useful life on the display device 130 of the controller 104. If the surgeon switches to a different mode of ablation, or a different energy setpoint within a mode of ablation, the calculated or estimated remaining useful life value will likewise change. That is, the value indicative of remaining useful life may be estimated or calculated assuming that the controller 104 remains operating in the current mode of ablation (and energy setpoint level) for the remaining useful life, but as the surgeon changes modes of ablation and/or energy setpoint level within the mode of ablation, the value indicative of remaining useful life will likewise change.

In yet still further embodiments, the value indicative of useful life may be checked, verified, or adjusted based on measured impedance. That is, the controller 104 may calculate or estimate remaining useful life during periods of time when plasma is present. When the impedance of the electrode circuit is measured (e.g., response to a command to create plasma, or perhaps automatically after cessation of plasma), the remaining useful life may be updated to reflect electrode wear. That, is, the calculate or estimated value indicative of remaining useful life may be increased if the measured impedance of the electrode circuit (when no plasma is present) indicates less wear than expected. Likewise, the calculate or estimated value indicative of remaining useful life may be decreased if the measured impedance of the electrode circuit (when no plasma is present) indicates more wear than expected. Moreover, the controller 104 may update the rates at which the value indicative of useful life is decremented during times when plasma is present based on actual rates calculated using two or more impedance measurements.

Figure 10:
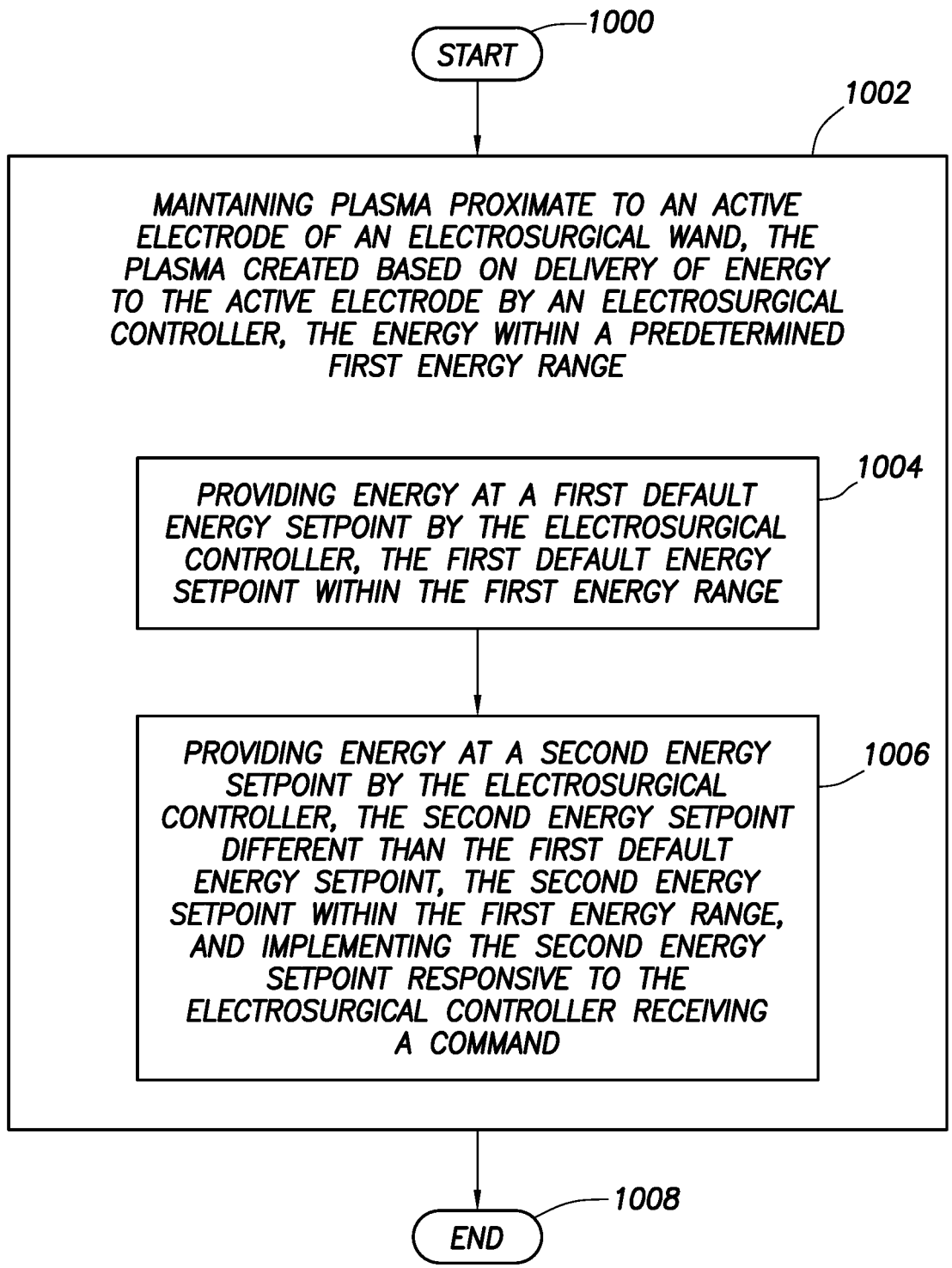
FIG. 10 shows a method in accordance with at least some embodiments.

FIG. 10 shows a method in accordance with some embodiments, portions or all of which may be implemented by a program executed on a processor. In particular, the method starts (block 1000) and proceeds to maintaining plasma proximate to an active electrode of an electrosurgical wand, the plasma created based on the delivery of output energy to the active electrode by an electrosurgical controller, the output energy within a predetermined first energy range (block 1002). During periods of time when output energy is being delivered within the first energy range, the method may comprise: providing output energy at a first default energy setpoint by the electrosurgical controller, the first default energy setpoint within the first energy range (block 1004); and providing output energy at a second energy setpoint by the electrosurgical controller, the second energy setpoint different than the first default energy setpoint, the second energy setpoint within the first energy range, and implementing the second energy setpoint responsive to the electrosurgical controller receiving a command (block 1006). Thereafter, the method ends (block 1008), possibly to be immediately restarted with a second energy range.

Figure 11:
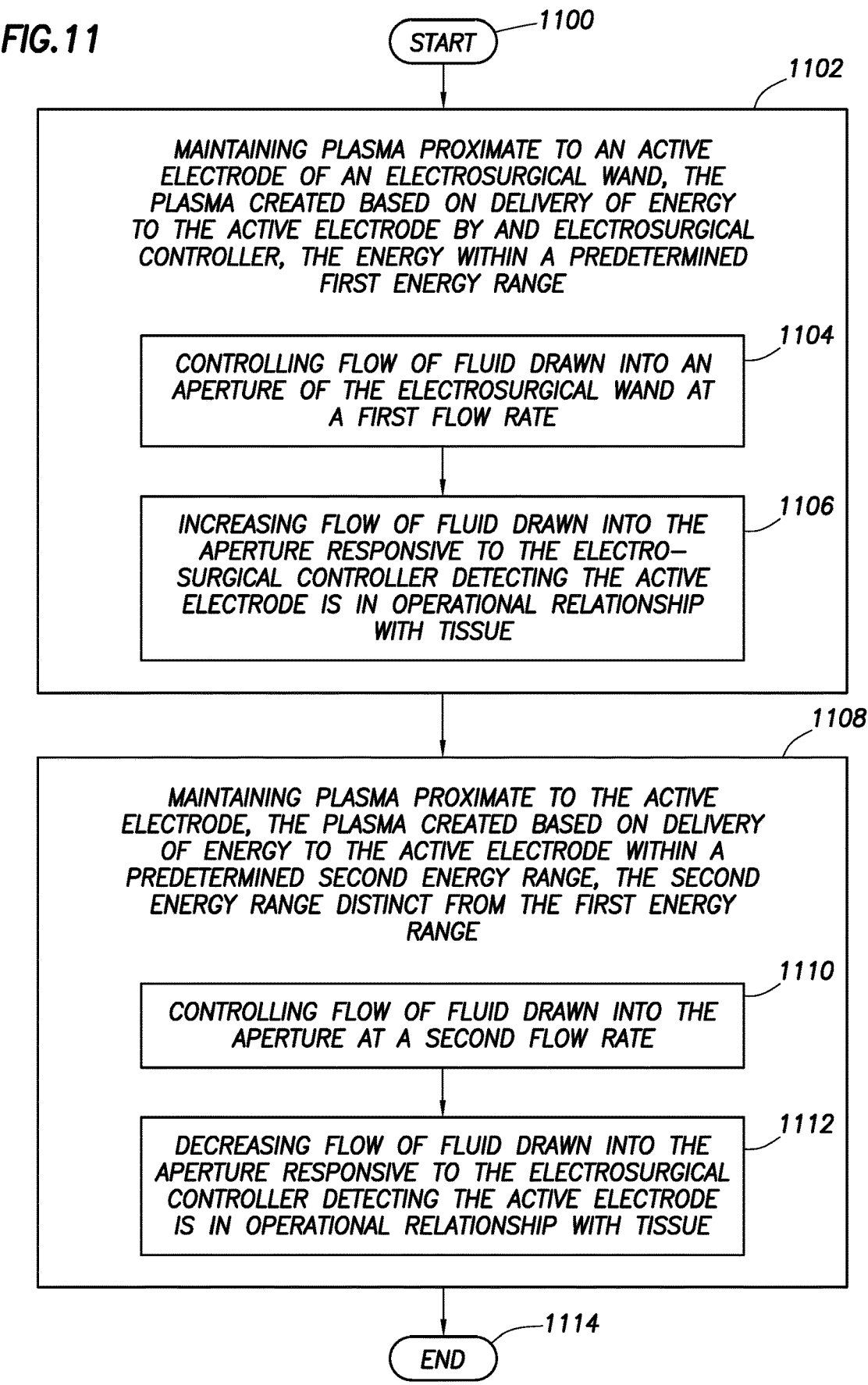
FIG. 11 shows a method in accordance with at least some embodiments.

FIG. 11 shows a method in accordance with some embodiments, portions or all of which may be implemented by a program executed on a processor. In particular, the method starts (block 1100) and proceeds to maintaining plasma proximate to an active electrode of an electrosurgical wand, the plasma created based on the delivery of output energy to the active electrode by an electrosurgical controller, the output energy within a predetermined first energy range (block 1102). During periods of time when output energy is being delivered within the first energy range, the method may comprise: controlling flow of fluid drawn into an aperture of the electrosurgical wand at a first flow rate (block 1104); and increasing flow of fluid drawn into the aperture responsive to the electrosurgical controller detecting the active electrode is in operational relationship with tissue (block 1106). Moreover, the method may comprise maintaining plasma proximate to the active electrode, the plasma created based on the delivery of output energy to the active electrode within a predetermined second energy range, the second energy range distinct from the first energy range (block 1108). During periods of time output energy is being delivered within the second energy range the method may comprise: controlling flow of fluid drawn into the aperture at a second flow rate (block 1110); and decreasing flow of fluid drawn into the aperture responsive to the electrosurgical controller detecting the active electrode is in operational relationship with tissue (block 1112). Thereafter, the method ends (block 1114), possibly to be immediately restarted.

The above discussion is meant to be illustrative of the principles and various embodiments of the present invention. Numerous variations and modifications are possible. It is intended that the following claims be interpreted to embrace all such variations and modifications.

While preferred embodiments of this disclosure have been shown and described, modifications thereof can be made by one skilled in the art without departing from the scope or teaching herein. The embodiments described herein are exemplary only and are not limiting. Because many varying and different embodiments may be made within the scope of the present inventive concept, including equivalent structures, materials, or methods hereafter thought of, and because many modifications may be made in the embodiments herein detailed in accordance with the descriptive requirements of the law, it is to be understood that the details herein are to be interpreted as illustrative and not in a limiting sense.

What is claimed is:

1. An electrosurgical controller for an electrosurgical wand comprising:
   a pump for controlling a flow of a fluid proximal to an active electrode of the electrosurgical wand; and
   a processor configured to control both an energy supplied by the electrosurgical controller and the pump, to create plasma proximate to the active electrode; and wherein in a first ablation mode, while supplying the energy, the processor is configured to control the pump based on a value indicative of an impedance of an electrode circuit comprising the active electrode to flow the fluid at a first flow rate that allows the plasma to collapse at uncontrolled intervals.

2. The electrosurgical controller of claim 1 wherein the processor is further configured to control the pump to operate in a second ablation mode, configured to flow the fluid at a second flow rate that avoids plasma collapse.

3. The electrosurgical controller of claim 1 wherein the electrode circuit includes at least one of: the plasma in operational relationship with the active electrode; conductive fluid surrounding the active electrode; a return electrode; and the electrode-fluid interfaces.

4. The electrosurgical controller of claim 1 wherein the value indicative of impedance is based on at least one of: the thickness of the plasma; the volume of the plasma; the surface area of the active electrode; and the volume flow of fluid and/or gasses away from the location of the plasma.

5. The electrosurgical controller of claim 1 wherein the processor is configured to control the pump to decrease the flow rate in response to a decrease in a value indicative of impedance of the electrode circuit corresponding to a lack of operational relationship with the tissue.

6. The electrosurgical controller of claim 1 wherein the processor is configured to control the pump to increase the flow rate of the fluid in response to an increase in the value indicative of impedance of the electrode circuit, corresponding to an operational relationship with the tissue.

7. The electrosurgical controller of claim 1 wherein the electrosurgical wand comprises an aspiration aperture and wherein the pump is operable to control an aspiration flow of fluid into the aspiration aperture.

8. The electrosurgical controller of claim 2 wherein the processor is configured to control the electrosurgical controller to deliver energy to the active electrode within a first energy range when in the first ablation mode, and to deliver energy to the active electrode within a second energy range when in the second ablation mode, wherein the second energy range is lower than the first energy range.

9. The electrosurgical controller of claim 8 wherein the processor is configured to control the pump to decrease the flow rate to stabilise the plasma formed proximate to the active electrode in response to a decrease in a value indication of impedance during periods of time when energy is being delivered in the second energy range.

10. The electrosurgical controller of any of claim 8 wherein each energy level comprises a plurality of energy setpoints.

11. The electrosurgical controller of claim 8 wherein: during periods of time when energy is being delivered within the first energy range, the electrosurgical controller is configured to control the pump to control the flow of fluid within a first flow rate range; and during periods of time when energy is being delivered within the second energy range, the electrosurgical controller is configured to control the pump to control the flow of fluid at a lower flow rate range.

12. The electrosurgical controller of claim 1 wherein the electrosurgical controller is configured to deliver the energy to the active electrode in the form of RF electrical current.

13. An electrosurgical controller for an electrosurgical wand comprising:
    a pump for controlling a flow of fluid proximal to an active electrode of the electrosurgical wand; and
    a processor configured to control the pump to control a plasma formed proximate to the active electrode, the plasma based on delivery of energy to the active electrode by the electrosurgical controller; and wherein the processor is configured to control the pump in a first mode to flow the fluid at a flow rate that causes regular but uncontrolled plasma collapse.

14. The electrosurgical controller of claim 13 wherein the processor is configured to control the pump based on an impedance of an electrode circuit comprising the active electrode.

15. The electrosurgical controller of claim 14 wherein the processor is configured to control the pump to decrease the flow of fluid through said electrosurgical wand in response to collapsed plasma.

16. The electrosurgical controller of claim 13 further comprising a voltage generator for providing the energy for delivery to the active electrode.

17. The electrosurgical controller of claim 13 wherein the processor is further configured to control the pump in a second mode, configured to avoid plasma collapse.

18. The electrosurgical controller of claim 17 wherein the first mode is configured so that more heat is dissipated into a target tissue, the heat dissipated during periods of plasma collapse, and wherein the second mode is configured so that less heat is dissipated into the target tissue.

* * * * *